United States Patent
Pascal et al.

(10) Patent No.: US 11,078,160 B2
(45) Date of Patent: Aug. 3, 2021

(54) ETHYNYL COMPOUNDS, THEIR PREPARATION AND THEIR THERAPEUTIC USE FOR THE TREATMENT OF MALARIA

(71) Applicant: SANOFI, Paris (FR)

(72) Inventors: Cécile Pascal, Craponne (FR); Alain Pellet, Sain Bel (FR); Gilles Courtemanche, Montrouge (FR); Simon Campbell, Poole (GB)

(73) Assignee: SANOFI, Paris (FR)

( * ) Notice: Subject to any disclaimer, the term of this patent is extended or adjusted under 35 U.S.C. 154(b) by 31 days.

(21) Appl. No.: 16/628,720

(22) PCT Filed: Jul. 4, 2018

(86) PCT No.: PCT/EP2018/068079
§ 371 (c)(1),
(2) Date: Jan. 6, 2020

(87) PCT Pub. No.: WO2019/008027
PCT Pub. Date: Jan. 10, 2019

(65) Prior Publication Data
US 2020/0281909 A1    Sep. 10, 2020

(30) Foreign Application Priority Data
Jul. 4, 2017 (EP) ..................................... 17305866

(51) Int. Cl.
| C07D 213/75 | (2006.01) |
| A61P 33/06 | (2006.01) |
| A61K 31/166 | (2006.01) |
| A61K 31/4402 | (2006.01) |

(52) U.S. Cl.
CPC .......... C07D 213/75 (2013.01); A61K 31/166 (2013.01); A61K 31/4402 (2013.01); A61P 33/06 (2018.01)

(58) Field of Classification Search
CPC ................................ C07D 213/75; A61P 33/06
See application file for complete search history.

(56) References Cited

FOREIGN PATENT DOCUMENTS

| EP | 2 727 911 | 5/2014 |
| WO | WO 2009/113092 | 9/2009 |
| WO | WO 2012/149093 | 11/2012 |

OTHER PUBLICATIONS

Abay, E. T. et al. "Efficacy and pharmacokinetic evaluation of a novel anti-malarial compound (NP046) in a mouse model" *Malaria Journal*, 2015, pp. 1-7, vol. 14, No. 8.
Krettli, A. U. et al. "The Search for New Antimalarial Drugs from Plants Used to Treat Fever and Malaria or Plants Ramdomly Selected: a Review" *Mem Inst Oswaldo Cruz*, Nov. 2001, pp. 1033-1042, vol. 96, No. 8.
Marfurt, J. et al. "Ex Vivo Drug Susceptibility of Ferroquine against Chloroquine-Resistant Isolates of *Plasmodium falciparum* and *P. vivax*" Antimicrobial Agents and Chemotherapy, Sep. 2011, 4461-4464, vol. 55, No. 9.
Written Opinion in International Application No. PCT/EP2018/068079, dated Aug. 9, 2018, pp. 1-6.

*Primary Examiner* — Golam M Shameem
(74) *Attorney, Agent, or Firm* — Saliwanchik, Lloyd & Eisenschenk

(57) ABSTRACT

The present disclosure relates to compounds of formula (I) or a pharmaceutically acceptable salt thereof wherein $R_1$ means a fluorine atom or a perhalogeno linear alkyl radical containing 1, 2 or 3 carbon atoms; $R_2$ means a chlorine atom, a linear alkyl radical containing 1, 2 or 3 carbon atoms or a perhalogeno linear alkyl radical containing 1, 2 or 3 carbon atoms, and R means a hydrogen atom or a radical of formula (Ia). The present disclosure also relates to processes for their preparation as well their therapeutic uses, in particular such as for use in the treatment of malaria.

15 Claims, No Drawings

ETHYNYL COMPOUNDS, THEIR PREPARATION AND THEIR THERAPEUTIC USE FOR THE TREATMENT OF MALARIA

CROSS-REFERENCE TO RELATED APPLICATION

This application is the U.S. national stage application of International Patent Application No. PCT/EP2018/068079, filed Jul. 4, 2018.

The present disclosure relates to new compounds and to their therapeutic use such as for use in the treatment of malaria.

INTRODUCTION

Malaria still remains a major health challenge in developing countries. According to the 2016 World malaria report from WHO (World Health Organization), and despite progress in the field, it was estimated that malaria affected 212 million people and killed 429 000 patients in 2015. Approximately, 70% of deaths have occurred in children aged less than five years old living in sub-Saharan Africa. Malaria is caused by protozoan parasites of the genus *Plasmodium* which are transmitted to humans by the bite of infected female Anopheles mosquitoes. *Plasmodium* infects and destroys red blood cells, leading to fever, severe anemia, cerebral malaria and, if untreated, death. *Plasmodium falciparum, Plasmodium vivax, Plasmodium ovale* and *Plasmodium malariae* are the four main species of *Plasmodium* responsible for the transmission of malaria. *Plasmodium falciparum* is the dominant species in sub-Saharan Africa, and the deadliest.

Since mid-twentieth century, a broad range of drugs has been developed and showed clinical efficacy for the treatment of uncomplicated falciparum malaria. To delay resistance development, WHO recommends since 2006 treatments based on combination of short-half-life artemisinin or derivatives (dihydroartemisinin, artemether, artesunate) with a long-lasting partner-drug including but not limited to lumefantrine, mefloquine, amiodiaquine, sulfadoxine, pyrimethamine or piperaquine. These combination therapies ally a fast onset of action and the capacity to target the erythrocytic life cycle of the parasite which is responsible for malaria symptoms. Unfortunately, despite the effectiveness of these Artemisinin-based Combination Therapy (ACTs), emergence of resistance has been observed in five countries of the Greater Mekong Sub-region resulting in a delayed parasite clearance linked to Kelch 13 propeller polymorphism. In Cambodia, high failure rates after treatment have been detected for four different ACTs.

Thus, the discovery of effective and affordable antimalarial agents with new mechanism of action is an imperative need to tackle malaria resistance. Besides, current ACTs are administered orally once or twice daily for three days but due to a low patient adherence, a lower effectiveness of ACTs is observed and is thought to be a major risk factor for development of drug resistance. Single dose treatment for uncomplicated malaria would have the potential to address multiple operational challenges of current treatment therapies. Compounds with pharmacokinetic properties supporting use in single-dose combination would be valuable in the fight against malaria.

Accordingly, this disclosure provides novel potent antimalarial agents that may prove to be effective anti-malarial in single dose to multiple dose cure.

SUMMARY OF THE DISCLOSURE

The present disclosure relates to novel compounds which are useful in the treatment and/or prophylaxis of uncomplicated malaria caused by *Plasmodium falciparum* and/or *Plasmodium vivax*.

Thus, the disclosure is directed to a compound of formula (I) as such or a pharmaceutically acceptable salt thereof as defined below in the detailed description:

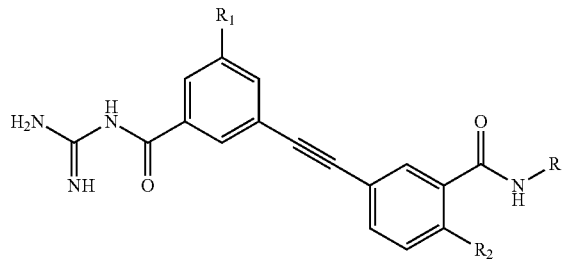

Formula (I)

The disclosure further relates to a pharmaceutical composition comprising at least one compound of formula (I) according to the disclosure or a pharmaceutically acceptable salt thereof, and at least one pharmaceutically acceptable carrier, diluent or excipient thereof.

Pharmaceutical compositions of the invention can contain one or more compound(s) of the invention in any form described herein.

Pharmaceutical compositions of this invention may further comprise one or more pharmaceutically acceptable additional ingredient(s), such as alum, stabilizers, antimicrobial agents, buffers, coloring agents, flavoring agents, adjuvants, and the like.

The disclosure further relates to processes for the preparation of a compound of formula (I) according to the invention or a pharmaceutically acceptable salt thereof, said processes being explained in detail below.

The disclosure further relates to a compound of formula (I) according to the invention or a pharmaceutically acceptable salt thereof for use as a medicament, such as for use in the prevention and/or treatment of malaria.

The disclosure further relates to a compound of formula (I) according to the invention or a pharmaceutically acceptable salt thereof for use in the treatment and/or prevention of infections of blood cells infected with *Plasmodium falciparum* and/or *Plasmodium vivax*.

According to a particular embodiment, the infection is malaria.

Thus, the disclosure further relates to a method for preventing and/or treating malaria in a patient in need thereof that comprises at least the administering of a compound of formula (I) according to the invention or a pharmaceutically acceptable salt thereof in a patient in need thereof.

Other features and advantages of the disclosure will be apparent from the following detailed description.

In the context of the disclosure, the following definitions apply:

The term "malaria" includes disease and conditions related to an infection by *Plasmodium*.

As used herein, the terms "treatment" and "treating" and the like generally mean obtaining a desired pharmacological and physiological effect. The effect may be prophylactic in terms of preventing or partially preventing the malaria or condition thereof and/or may be therapeutic in terms of a partial or complete cure of a disease, condition, symptom or adverse effect attributed to the disease. The term "treatment" as used herein covers any treatment of the malaria in a mammal, particularly a human, and includes: (a) preventing the malaria from occurring in a subject which may be predisposed to the malaria but has not yet been diagnosed as having it; (b) inhibiting the disease, i.e., arresting its development; or relieving the disease, i.e., causing regression of the disease and/or its symptoms or conditions.

The term "effective amount" includes "prophylaxis-effective amount" as well as "treatment-effective amount".

The term "prophylaxis-effective amount" refers to a concentration of compound of this invention that is effective in inhibiting, decreasing the likelihood of the disease by malarial parasites, or preventing malarial infection or preventing the delayed onset of the disease by malarial parasites, when administered before infection, i.e. before, during and/or slightly after the exposure period to malarial parasites.

The term "prophylaxis" includes causal prophylaxis, i.e. antimalarial activity comprising preventing the pre-erythrocytic development of the parasite, suppressive prophylaxis, i.e. antimalarial activity comprising suppressing the development of the blood stage infection and terminal prophylaxis, i.e. antimalarial activity comprising suppressing the development of intra-hepatic stage infection. This term includes primary prophylaxis (i.e. preventing initial infection) where the antimalarial compound is administered before, during and/or after the exposure period to malarial parasites and terminal prophylaxis (i.e. to prevent relapses or delayed onset of clinical symptoms of malaria) when the antimalarial compound is administered towards the end of and/or slightly after the exposure period to malarial parasites but before the clinical symptoms. Typically, against *P. falciparum* infections, suppressive phophylaxis is used whereas against *P. vivax*, terminal prophylaxis is used.

Likewise, the term "treatment-effective amount" refers to a concentration of compound that is effective in treating malaria infection, e.g. leads to a reduction in parasite numbers in blood following microscopic examination when administered after infection has occurred.

The term "subject" as used herein refers to mammals. For examples, mammals contemplated by the present disclosure include humans and the like.

DETAILED DESCRIPTION OF THE INSTANT DISCLOSURE

Compounds of the Disclosure

The present disclosure relates to novel compounds of formula (I) as such:

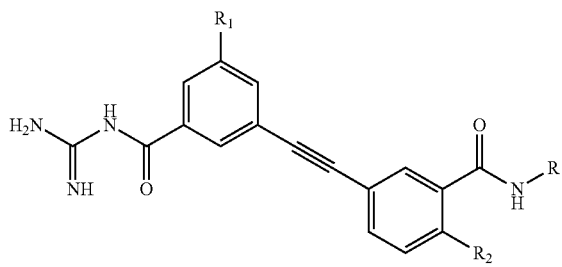

Formula (I)

wherein:
$R_1$ means a fluorine atom or a perhalogeno linear alkyl radical containing 1, 2 or 3 carbon atoms such as a trifluoromethyl radical,
$R_2$ means a chlorine atom; a linear alkyl radical containing 1, 2 or 3 carbon atoms optionally substituted with at least one fluorine atom, such as a methyl radical; or a perhalogeno linear alkyl radical containing 1, 2 or 3 carbon atoms such as a trifluoromethyl radical, and
R means a hydrogen atom or a radical of formula (Ia)

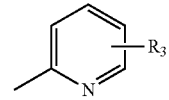

Formula (Ia)

wherein $R_3$ means a hydrogen atom; a hydroxyl radical; or a linear or branched alkyl radical containing 1, 2 or 3 carbon atoms, such as a methyl radical,
and $R_3$ is in position 5 or in position 6 of said radical of formula (Ia),
or a pharmaceutically acceptable salt thereof.

In the context of the disclosure, the following definitions apply:

«pharmaceutically acceptable salt thereof» refers to salts which are formed from acid addition salts formed with an acid (also stated as AH in the instant disclosure), said acid may be an inorganic acid (e.g. hydrochloric acid, hydrobromic acid, sulfuric acid, phosphoric acid, nitric acid, and the like), or an organic acid such as acetic acid, fumaric acid, oxalic acid, tartaric acid, succinic acid, malic acid, malonic acid, fumaric acid, maleic acid, ascorbic acid, lactic acid, mandelic acid, benzoic acid, tannic acid, palmoic acid, alginic acid, polyglutamic acid, para-toluene sulfonic acid, benzene sulfonic acid, methane sulfonic acid, naphthalene sulfonic acid, naphthalene disulfonic acid, and poly-galacturonic acid.

Pharmaceutically acceptable salts for the instant disclosure may be selected among salts formed with acids such as hydrochloric acid, fumaric acid, succinic acid and malonic acid.

"a halogen atom" refers to a fluorine, chlorine, bromine or iodine atom. Fluorine or chlorine atom may be selected as a halogen atom.

"an alkyl radical" refers to a carbon-based chain of 1 to 3 carbon atoms, such as methyl, ethyl, propyl, isopropyl radicals.

the expression "$R_3$ is in position 5 or in position 6 of said radical of formula (Ia)" (that is to say in position 5 or in position 6 of the pyridine-2-yl ring) means that $R_3$ is linked to the pyridine-2-yl ring according to the two alternatives as shown below:

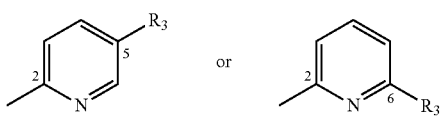

According to one embodiment, distinguished compounds are those of formula (I) wherein $R_1$ means a fluorine atom or a trifluoromethyl radical.

According to another embodiment, distinguished compounds are those of formula (I) wherein $R_2$ means a chlorine atom, a methyl radical or a perhalogeno linear alkyl radical containing 1, 2 or 3 carbon atoms such as a trifluoromethyl radical.

According to one embodiment, distinguished compounds are those of formula (I) wherein R means a radical of formula (Ia) as defined above.

According to another embodiment, distinguished compounds are those of formula (I) wherein R means a hydrogen atom.

According to another embodiment distinguished compounds are those of formula (I) wherein R means a radical of formula (Ia) as defined above and $R_3$ is in position 5 or 6 of said radical of formula (Ia).

According to another embodiment, distinguished compounds are those of formula (I) wherein R means a radical of formula (Ia) as defined above and $R_3$ means a hydrogen atom, a hydroxyl radical or a linear or branched alkyl radical containing 1, 2 or 3 carbon atoms.

According to another embodiment, distinguished compounds are those of formula (I) wherein R means a radical of formula (Ia) as defined above and $R_3$ means a hydrogen atom, a hydroxyl radical or a methyl radical.

According to another embodiment, distinguished compounds are those of formula (I) wherein R means a radical of formula (Ia) as defined above and $R_3$ means a hydroxyl radical in position 5 of said radical of formula (Ia).

According to another embodiment, distinguished compounds are those of formula (I) wherein R means a radical of formula (Ia) as defined above and $R_3$ means a linear or branched alkyl radical containing 1, 2 or 3 carbon atoms in position 6 of said radical of formula (Ia).

According to another embodiment, distinguished compounds are those of formula (I) wherein R means a radical of formula (Ia) as defined above and $R_3$ means a methyl radical in position 6 of said radical of formula (Ia).

According to another embodiment, distinguished compounds are those of formula (I) wherein at least one of $R_1$ and $R_2$ means a perfluoromethyl radical.

According to another embodiment, distinguished compounds are those of formula (I) in which at least one of $R_1$ and $R_2$ means a perfluoromethyl radical and R means a radical of formula (Ia) as defined above.

According to another embodiment, distinguished compounds are those of formula (I) wherein at least one of $R_1$ and $R_2$ means a perfluoromethyl radical, R means a radical of formula (Ia) and $R_3$ is in position 5 or 6 of said radical of formula (Ia).

According to another embodiment, distinguished compounds are those of formula (I) wherein $R_1$ and $R_2$ both mean a perfluoromethyl radical.

According to another embodiment, distinguished compounds are those of formula (I) wherein $R_1$ and $R_2$ both mean a perfluoromethyl radical and R means a radical of formula (Ia) as defined above.

According to another embodiment, distinguished compounds are those of formula (I) wherein $R_1$ and $R_2$ both mean a perfluoromethyl radical, R means a radical of formula (Ia) as defined above and $R_3$ is in position 5 or 6 of said radical of formula (Ia).

According to another embodiment, distinguished compounds are those of formula (I) wherein $R_1$ means a fluorine atom or a trifluoromethyl radical, $R_2$ means a trifluoromethyl radical, a methyl radical or a chlorine atom, R means a hydrogen atom or a radical of formula (Ia) as defined above and $R_3$ is in position 5 or 6 of said radical of formula (Ia) and is a hydrogen atom, a methyl radical or a hydroxyl radical.

The embodiments and the various combinations emerging therefrom are clearly illustrated by the compounds and examples below.

Among the compounds of formula (I) and salified form (II) that are subject-matters of the instant disclosure, mention may be made of the compounds selected from the following list:

5-((3-(carbamimidoylcarbamoyl)-5-(trifluoromethyl)phenyl)ethynyl)-N-(pyridin-2-yl)-2-(trifluoromethyl)benzamide, 5-((3-(carbamimidoylcarbamoyl)-5-(trifluoromethyl)phenyl)ethynyl)-N-(pyridin-2-yl)-2-(trifluoromethyl)benzamide, 5-((3-(carbamimidoylcarbamoyl)-5-(trifluoromethyl)phenyl)ethynyl)-N-(pyridin-2-yl)-2-(trifluoromethyl)benzamide, 5-((3-((diaminomethylene)carbamoyl)-5-(trifluoromethyl)phenyl)ethynyl)-2-methyl-N-(6-methylpyridin-2-yl)benzamide, 5-((3-(carbamimidoylcarbamoyl)-5-fluorophenyl)ethynyl)-N-(6-methylpyridin-2-yl)-2-(trifluoromethyl)benzamide, 5-((3-(carbamimidoylcarbamoyl)-5-trifluoromethyl)phenyl)ethynyl)-2-methyl-N-(pyridin-2-yl)benzamide, 5-((3-(carbamimidoylcarbamoyl)-5-(trifluoromethyl)phenyl)ethynyl)-N-(5-hydroxypyridin-2-yl)-2-(trifluoromethyl)benzamide, 5-((3-(carbamimidoylcarbamoyl)-5-(trifluoromethyl)phenyl)ethynyl)-2-chloro-N-(pyridin-2-yl)benzamide, 5-((3-(carbamimidoylcarbamoyl)-5-fluorophenyl)ethynyl)-N-(pyridin-2-yl)-2-(trifluoromethyl)benzamide, N-carbamimidoyl-3-((3-carbamoyl-4-(trifluoromethyl)phenyl)ethynyl)-5-trifluoromethyl)benzamide, and their pharmaceutically acceptable salts.

In the present disclosure, the pharmaceutically acceptable salt may be formed from an acid addition salt which is formed with an acid, said acid being an inorganic acid, preferably chosen among hydrochloric acid, hydrobromic acid, sulfuric acid, phosphoric acid, and nitric acid, more preferably hydrochloric acid, or an organic acid, preferably chosen among acetic acid, fumaric acid, oxalic acid, tartaric acid, succinic acid, malic acid, malonic acid, fumaric acid, maleic acid, ascorbic acid, lactic acid, mandelic acid, benzoic acid, tannic acid, palmoic acid, alginic acid, polyglutamic acid, para-toluene sulfonic acid, benzene sulfonic acid, methane sulfonic acid, naphthalene sulfonic acid, naphthalene disulfonic acid, and poly-galacturonic acid, more preferably chosen among fumaric acid, succinic acid and malonic acid.

Among their salts mention may be made especially of the salts selected from the following list:

5-((3-(carbamimidoylcarbamoyl)-5-(trifluoromethyl)phenyl)ethynyl)-N-(pyridin-2-yl)-2-(trifluoromethyl)benzamide hydrochloride, 5-((3-(carbamimidoylcarbamoyl)-5-(trifluoromethyl)phenyl)ethynyl)-N-(pyridin-2-yl)-2-(trifluoromethyl)benzamide malonic acid, 5-((3-((diaminomethylene)carbamoyl)-5-(trifluoromethyl)phenyl)ethynyl)-2-methyl-N-(6-methylpyridin-2-yl)benzamide hydrochloride, 5-((3-(carbamimidoylcarbamoyl)-5-fluorophenyl)ethynyl)-N-(6-methylpyridin-2-yl)-2-(trifluoromethyl)benzamide hydrochloride, 5-((3-(carbamimidoylcarbamoyl)-5-trifluoromethyl)phenyl)ethynyl)-2-methyl-N-(pyridin-2-yl)benzamide hydrochloride, 5-((3-(carbamimidoylcarbamoyl)-5-(trifluoromethyl)phenyl)ethynyl)-N-(5-hydroxypyridin-2-yl)-2-(trifluoromethyl)benzamide hydrochloride, 5-((3-(carbamimidoylcarbamoyl)-5-(trifluoromethyl)phenyl)ethynyl)-2-chloro-N-(pyridin-2-yl)benzamide hydrochloride, and 5-((3-(carbamimidoylcarbamoyl)-5-fluorophenyl)ethynyl)-N-(pyridin-2-yl)-2-(trifluoromethyl)benzamide hydrochloride.

The previously detailed compounds are listed in Table 1 below. It should be noted that the above compounds have been named according to the IUPAC nomenclature using the software Perkin Elmer ChemLabNoteBook.

TABLE 1

| FORMULA | COMPOUND NO | IUPAC NAME |
|---|---|---|
| | 1a | 5-((3-(carbamimidoylcarbamoyl)-5-(trifluoromethyl)phenyl)ethynyl)-N-(pyridin-2-yl)-2-(trifluoromethyl)benzamide |
| | 1b | 5((3-(carbamimidoylcarbamoyl)-5-(trifluoromethyl)phenyl)ethynyl)-N-(pyridin-2-yl)-2-(trifluoromethyl)benzamide hydrochloride |
| | 1c | 5((3-(carbamimidoylcarbamoyl)-5-(trifluoromethyl)phenyl)ethynyl)-N-(pyridin-2-yl)-2-(trifluoromethyl)benzamide malonic acid |
| | 2 | 5-((3-((diaminomethylene)carbamoyl)-5-(trifluoromethyl)phenyl)ethynyl)-2-methyl-N-(6-methylpyridin-2-yl)benzamide hydrochloride |

TABLE 1-continued

| FORMULA | COMPOUND NO | IUPAC NAME |
|---|---|---|
| 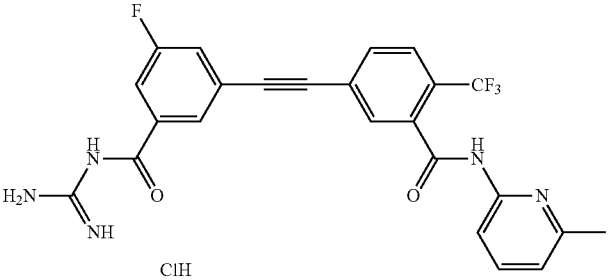 [SMILES: Cc1cccc(NC(=O)c2cc(C#Cc3cc(F)cc(C(=O)NC(=N)N)c3)ccc2C(F)(F)F)n1 ; Cl] | 3 | 5-((3-(carbamimidoylcarbamoyl)-5-fluorophenyl)ethynyl)-N-(6-methylpyridin-2-yl)-2-(trifluoromethyl)benzamide hydrochloride |
| 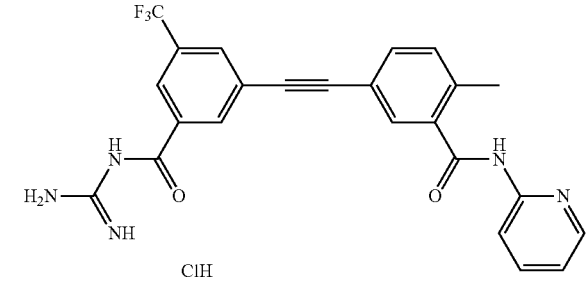 [SMILES: Cc1ccc(C#Cc2cc(C(=O)NC(=N)N)cc(C(F)(F)F)c2)cc1C(=O)Nc1ccccn1 ; Cl] | 4 | 5-((3-(carbamimidoylcarbamoyl)-5-trifluoromethyl)phenyl)ethynyl)-2-methyl-N-(pyridin-2-yl)benzamide hydrochloride |
| 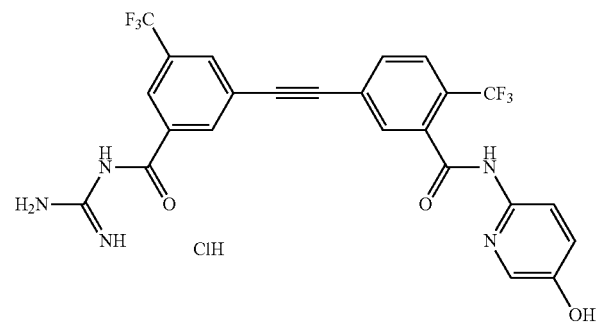 [SMILES: N=C(N)NC(=O)c1cc(C#Cc2ccc(C(F)(F)F)c(C(=O)Nc3ccc(O)cn3)c2)cc(C(F)(F)F)c1 ; Cl] | 5 | 5-((3-(carbamimidoylcarbamoyl)-5-(trifluoromethyl)phenyl)ethynyl)-N-(5-hydroxypyridin-2-yl)-2-(trifluoromethyl)benzamide hydrochloride |
| 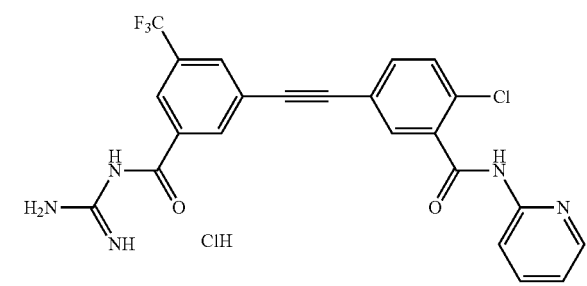 [SMILES: N=C(N)NC(=O)c1cc(C#Cc2ccc(Cl)c(C(=O)Nc3ccccn3)c2)cc(C(F)(F)F)c1 ; Cl] | 6 | 5-((3-(carbamimidoylcarbamoyl)-5-(trifluoromethyl)phenyl)ethynyl)-2-chloro-N-(pyridin-2-yl)benzamide hydrochloride |
| 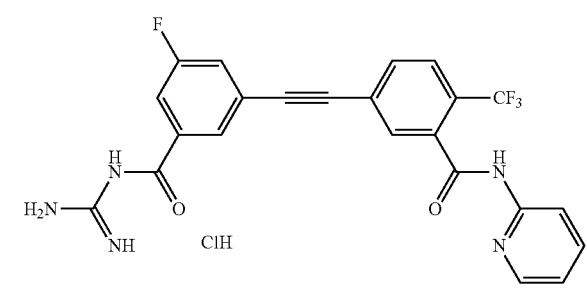 [SMILES: N=C(N)NC(=O)c1cc(F)cc(C#Cc2ccc(C(F)(F)F)c(C(=O)Nc3ccccn3)c2)c1 ; Cl] | 7 | 5-((3-(carbamimidoylcarbamoyl)-5-fluorophenyl)ethynyl)-N-(pyridin-2-yl)-2-(trifluoromethyl)benzamide hydrochloride |

TABLE 1-continued

| FORMULA | COMPOUND NO | IUPAC NAME |
|---|---|---|
| | 8 | N-carbamimidoyl-3-((3-carbamoyl-4-(trifluoromethyl)phenyl)ethynyl)-5-trifluoromethyl)benzamide |

Among the previous compounds of Table 1 mention may be made of the compounds No 1a, 1b, 1c, 2, 3, 4, 5, 6, 7, and 8.

Among the previous compounds mention may be made of the compounds no 1a, 1b, 1c and 4.

Method of Preparation

The compounds of formula (I) can be prepared from readily available starting materials using methods and procedures known from the skilled person. It will be appreciated that where typical or preferred experimental conditions (i.e. reaction temperatures, time, moles of reagents, solvents etc.) are given, other experimental conditions can also be used unless otherwise stated.

Optimum reaction conditions may vary with the particular reactants or solvents used, but such conditions can be determined by the person skilled in the art, using routine optimisation procedures.

As detailed here-after, the compounds of formula (I) may be obtained from a compound of formula (V) as defined here-after, which may be prepared according to two different routes.

Both general synthetic approaches for obtaining compounds of formula (I) and salified form (II) are depicted in Scheme 1 and Scheme 4 below.

In the foregoing, the starting compounds and the reagents, when their preparation method is not described, are commercially available or described in the literature, or else may be prepared according to methods that are described therein or that are known to those skilled in the art.

Scheme 1

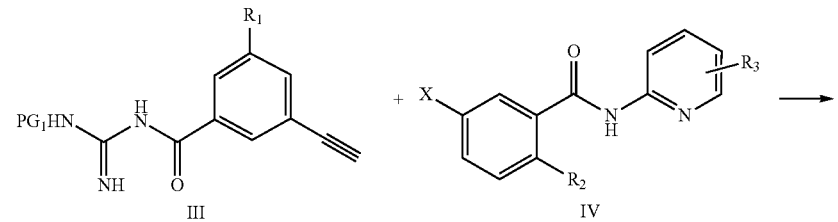

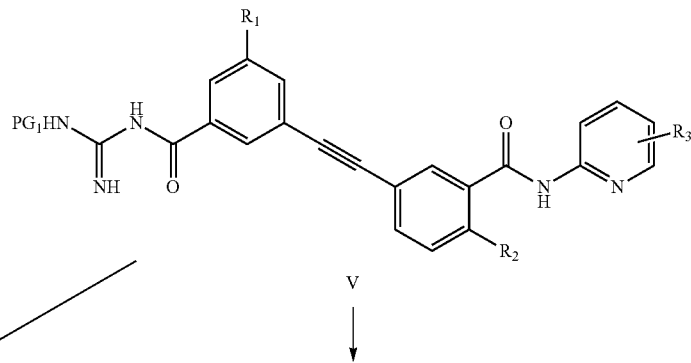

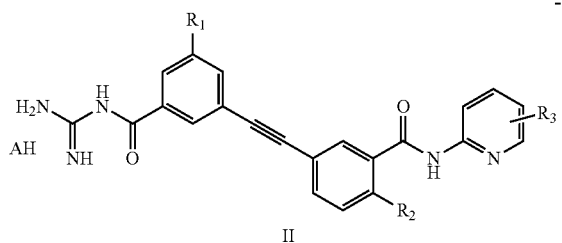

II

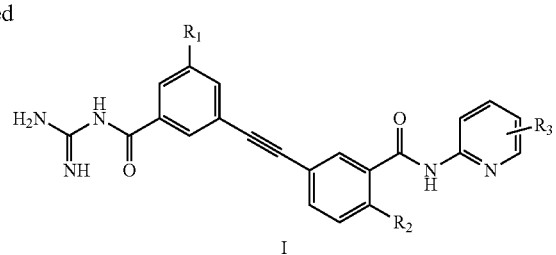

I

Thus, the present disclosure is also directed to a process for the preparation of a compound of formula (I) or a pharmaceutically acceptable salt thereof according to the invention comprising at least the following step consisting in:

a catalytic coupling, in particular with a Palladium catalyst, between an intermediate compound of formula (III)

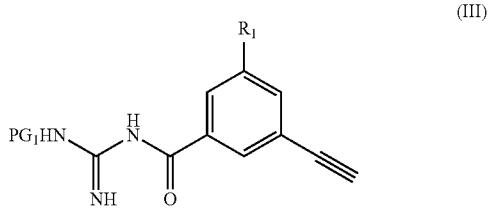

wherein:

PG$_1$ is a conventional amine protecting group, in particular as defined here-after and R$_1$ means a fluorine atom or a perhalogeno linear alkyl radical containing 1, 2 or 3 carbon atoms such as a trifluoromethyl radical;

and an intermediate compound of formula (IV)

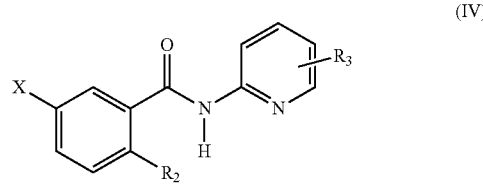

wherein

R$_2$ and R$_3$ are as defined in formula (I) and X is a bromine atom or an iodine atom;

so as to obtain a compound of formula (V)

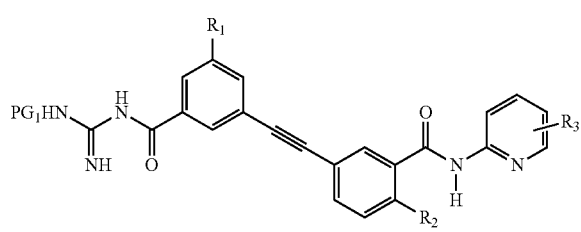

wherein R$_1$, R$_2$, R$_3$ and PG$_1$ are as defined above,
said compound of formula (V) being further deprotected and optionally salified to form the expected compound of formula (I) according to the invention or a pharmaceutically acceptable salt thereof.

Regarding the step of coupling between compounds of formulae (III) and (IV), it is also known as a Sonogashira coupling. It generally involves as catalyst, a palladium catalyst such as bis(triphenylphosphine)palladium(II) dichloride, [1,1'-bis(diphenylphosphino)ferrocene]dichloropalladium(II), bis(dibenzylideneacetone)palladium, palladium(II) diacetate or tetrakistriphenylphosphine palladium, optionally in presence of a copper(I) cocatalyst such as cuprous iodide or bromide in presence of palladium catalyst such as bis(triphenylphosphine)palladium(II) dichloride or tetrakistriphenylphosphine palladium, a copper(I) cocatalyst such as cuprous iodide or bromide. In particular, such a catalytic coupling may be realized in an anhydrous organic solvent such as dimethylformamide, ethylacetate, dimethylacetamide, toluene, tetrahydrofuran, or acetonitrile, and in presence of an amine base such as triethylamine, diisopropylamine, morpholine or piperidine and an additional ligand such as triphenylphosphine or tri-tert-butylphosphine. The reaction may be performed, for instance in a sealed tube. The so-formed reaction mixture may be degassed and heated at 40° C. to 70° C. until achievement of the reaction. The completion of reaction may be controlled by TLC (thin layer chromatography). For the recovery of the compound (V), the reaction mixture may be advantageously allowed to cool to room temperature, diluted, and filtered through celite bed. The so obtained filtrate may be then concentrated in vacuum and if necessary purified before performing the following steps. The compound (V) could also be directly crystallized from the reaction mixture and recovered by filtration.

The group PG$_1$ of compound of formula (III) and of the so-obtained compound of formula (V) is a conventional amine protecting group that firstly protects the amine reactive function which is then secondly regenerated into the amine reactive function in another step of the chemical synthesis of the compounds (I).

Examples of protecting groups and also protection and deprotection methods are given in *Protective Groups in Organic Synthesis*, Greene et al., 4th Edition (John Wiley & Sons, Inc., New York), 2007. For instance, PG$_1$ corresponds to a tert-butoxy carbonyl radical (Boc) or a benzyl carbonyl radical (Cbz).

The step of deprotection of the thus obtained compound of formula (V) may be performed by a convenient route known by the man skilled in the art. For instance, it may be realized in presence of an acid such as concentrated hydrochloride or hydrochloride in diethyl ether with ice cooling, or in presence of an acid such as trifluoroacetic acid or paratoluenesulfonic acid in a solvent such as ethyl acetate (AcOet) or dichloromethane in order to obtain either a compound of formula (I) as defined previously or a pharmaceutically acceptable salt thereof which is a compound of formula (II)

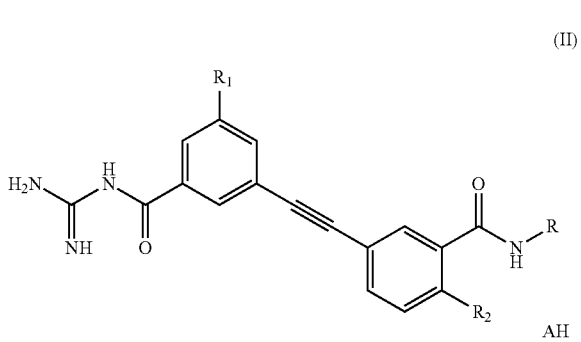

wherein
$R_1$ and $R_2$ are as defined above;
R means a hydrogen atom or a radical of formula (Ia)

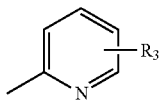

Formula (Ia)

$R_3$ being as defined above; and
AH is an acid.

When $PG_1$ is a conventional protecting group as defined above such as a tert-butoxy carbonyl radical (Boc), the acylguanidine deprotection step of the derivative formula (V) may be performed in presence of an acid such as concentrated hydrochloride or hydrochloride in diethyl ether with ice cooling. The precipitated solid may be then isolated, washed with water and dried to obtain compound (II) as a hydrochloride salt of compound (I).

The acylguanidine deprotection step of the derivative of formula (V) may be achieved with trifluoroacetic acid or para toluene sulfonic acid in a solvent such as ethyl acetate (AcOEt) or dichloromethane with heating up to 70° C. Once the deprotection step achieved, the medium may be then basified with a base such as an ammonium hydroxide or sodium hydroxide under cooling and until pH=9-10. After washing of the organic phase with for instance water then with for instance aqueous solution of sodium metabisulfite and treatment with active charcoal, the organic solution of compound is partially concentrated.

When the compound obtained at the end of the deprotection step is a compound of formula (I), if needed a salification may be performed by adding a solution of an acid such as malonic acid, fumaric acid or succinic acid in an organic solvent such as ethylacetate or tetrahydrofuran of the thus obtained compound (I) from step (2) to obtain the pharmaceutically acceptable salt of formula (II) wherein $R_1$, $R_2$, $R_3$, R and AH are as defined above.

The salification may be performed by adding a solution of an acid in an organic solvent such as ethylacetate or tetrahydrofuran such as malonic acid or succinic acid to form a compound (II) as a malonate salt of compound (I).

Regarding the starting materials (III) and (IV), they may be easily produced by a man skilled in the art, in particular according to the methods of preparation submitted in the following examples.

In particular, the starting material (III) with $R_1$ as defined previously, may be prepared according to the following scheme 2.

Scheme 2

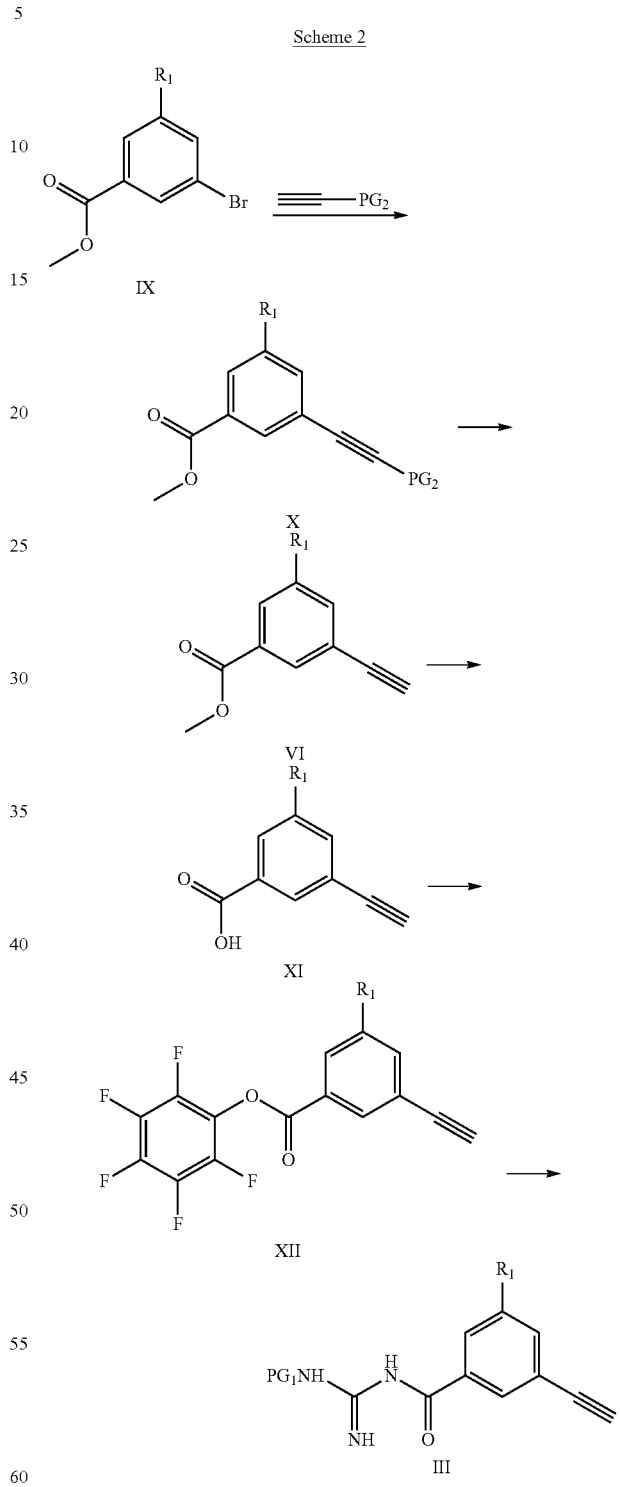

In a first step, a Sonogashira coupling is performed between the compounds (IX) and a protected acetylene ($PG_2$-acetylene) wherein $R_1$ is as defined previously and $PG_2$ is a conventional protecting group different from the protecting group $PG_1$. For instance, $PG_2$ corresponds to a trimethylsilyl radical (TMS) or a triethylsilyl radical (TES).

This coupling reaction may be performed as detailed for the previous coupling between compounds (III) and (IV).

When $PG_2$ is TMS, the acetylene deprotection step of the derivative formula (X) is performed in presence of a base such as potassium carbonate, lithium hydroxide or potassium hydroxide in a solvent such as methanol or tetra-n-butyl ammonium fluoride in dichloromethane from 0° C. to room temperature. If a $PG_2$ other than TMS is used, the deprotection step is accordingly adapted (see: *Protective Groups in Organic Synthesis*, Greene et al., 4th Edition (John Wiley & Sons, Inc., New York), 2007. After concentration and work-up, the crude compound (VI) may be used directly to obtain compound (XI).

The formation of compound (VI) is achieved with a base such as lithium hydroxide or sodium hydroxide in a solvent such as methanol or tetrahydrofuran in water. After concentration and acidification with an acid such as hydrochloride 1N in water or solution of citric acid in water, the obtained precipitate is collected and washed with water and dried to give compound (XI).

The activation of acidic group of compound (XI) can be achieved using a coupling reagent such as dicyclohexylcarbodiimide or benzotriazol-1-yl-oxytripyrrolidinophosphonium hexafluorophosphate in presence of pentafluorophenol in a solvent such as tetrahydrofuran or dimethylformamide from 0° C. to 50° C. After cooling, and removal of precipitated urea, the filtrate is concentrated and purified to give compound (XII).

The last step to obtain compound (III) may be performed by adding protected guanidine with for instance tert-butoxycarbonyl group, to compound (XII) in a solvent such as tetrahydrofuran or dimethylformamide from 0° C. to 50° C. After completion of the reaction and work-up, the crude residue is purified to give compound (III).

The disclosure further describes an intermediate compound of formula (III) as such

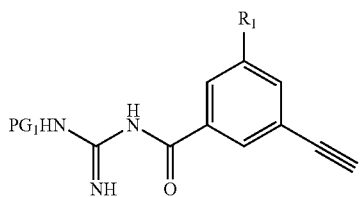

wherein $PG_1$ is a conventional amine protecting group that firstly protects the amine reactive function which is then secondly regenerated into the amine reactive function in another step of the chemical synthesis of the compounds (I). As mentioned above, examples of protecting groups and also protection and deprotection methods are given in *Protective Groups in Organic Synthesis*, Greene et al., 4th Edition (John Wiley & Sons, Inc., New York), 2007. $PG_1$ corresponds to a tert-butoxy carbonyl radical (Boc) or a benzyl carbonyl radical (Cbz); and $R_1$ means a fluorine atom or a perhalogeno linear alkyl radical containing 1, 2 or 3 carbon atoms such as a trifluoromethyl radical.

Among the compounds of formula (III) may be cited the following specific compounds:

tert-butyl N—[N-[3-ethynyl-5-(trifluoromethyl)benzoyl] carbamimidoyl]carbamate, and N—[N-(3-ethynyl-5-fluoro-benzoyl)carbamimidoyl]carbamate.

Regarding the starting material (IV), different ways of preparation may be considered according to the possible definitions for $R_2$, $R_3$, and X.

Thus, when $R_2$=$CF_3$ or Cl and X=Br this starting material (IV) could be synthetized with the following scheme 3.

Scheme 3

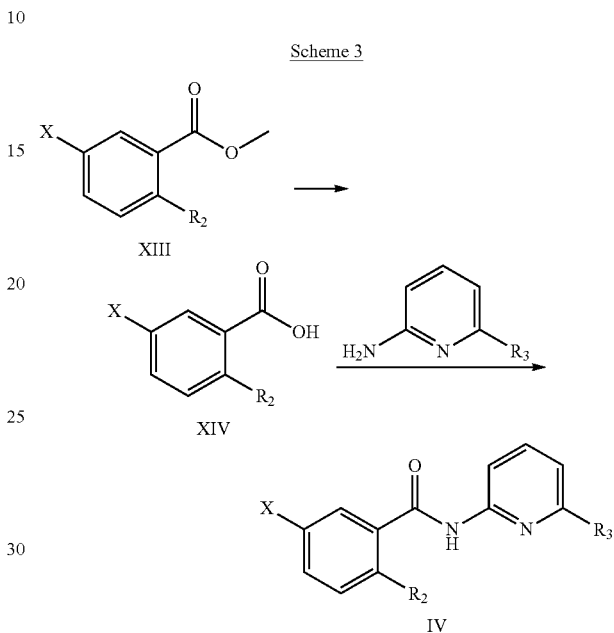

Formation of compound (XIII) is achieved as previously described for compound (XI) to give compound (XIV).

The acidic group of compound (XIV) is converted to acyl chloride with thionylchloride, phosphorous oxychloride or oxalyl chloride in an inert solvent such as toluene or dichloromethane from 0° to 50° C. After completion of the reaction and concentration, the crude compound (XIV) is diluted with a solvent such as ethylacetate or dichloromethane and 2-aminopyridine (XV) is added in presence of a base such as trimethylamine, pyridine or diisopropylethylamine from 0° C. to room temperature. The reaction mixture may be kept under stirring until achievement of the reaction. After work-up, the crude residue is purified to give compound (IV).

The disclosure further describes an intermediate compound of formula (IV) as such

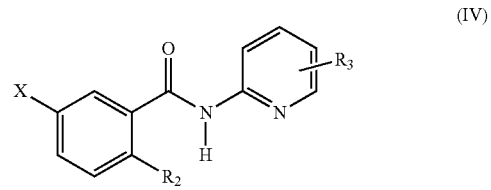

wherein $R_2$ means a chlorine atom; a linear alkyl radical containing 1, 2 or 3 carbon atoms optionally substituted with at least one fluorine atom, such as a methyl radical; or a perhalogeno linear alkyl radical containing 1, 2 or 3 carbon atoms such as a trifluoromethyl radical, R<sub>3</sub> means a hydrogen atom; a hydroxyl radical; or a linear or branched alkyl radical containing 1, 2 or 3 carbon atoms, such as a methyl radical, R<sub>3</sub> being in position 5 or in position 6 of the pyridine-2-yl ring, and X is a bromine atom or an iodine atom.

Among the compounds of formula (IV) may be cited the following specific compounds:

5-Bromo-N-pyridin-2-yl-2-trifluoromethyl-benzamide, 5-bromo-2-methyl-N-(6-methylpyridin-2-yl)benzamide, 5-bromo-N-(6-methylpyridin-2-yl)-2-(trifluoromethyl)benzamide, 5-iodo-2-methyl-N-(pyridin-2-yl)benzamide, 5-Bromo-N-(5-hydroxy-pyridin-2-yl)-2-trifluoromethyl-benzamide, and 5-bromo-2-chloro-N-(pyridin-2-yl)benzamide.

In particular, the starting material (XIII) wherein R<sub>2</sub> means a CF<sub>3</sub> radical, is synthetized according to the following scheme a.

Scheme a

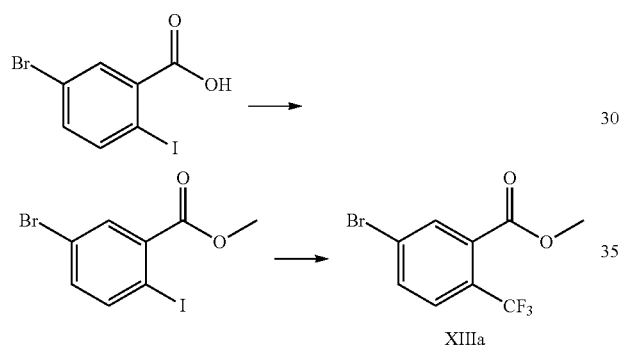

XIIIa

Esterification of 5-bromo-2-iodobenzoic acid may be performed using an acid such as sulfuric acid in presence of methanol.

Then the next step may consist in introducing a trifluoromethyl group using methyl 2,2-difluoro-2-(fluorosulfonyl)acetate in presence of copper iodide or copper bromide in N-methylpyrrolidinone or dimethylformamide. The reaction mixture may be heated from 80° C. to 120° C. Once completion achieved and after work-up, the crude residue is purified to give compound (XIIIa).

Regarding the starting material (IV) having R<sub>3</sub>=OH in position 5 of the pyridine-2-yl group and X=Br, it could be synthetized according to the following scheme b.

Scheme b

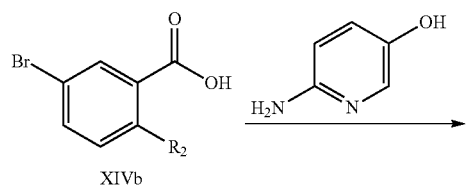

XIVb

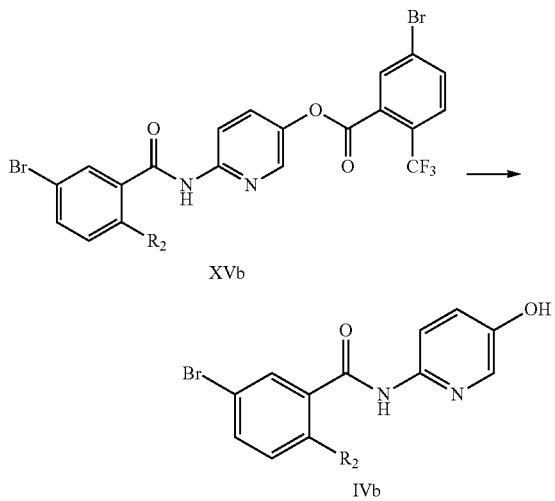

XVb

IVb

Compound (XVb) wherein R<sub>2</sub> is as defined previously is formed using the same procedure as for compound (IV).

Compound (IVb) wherein R<sub>2</sub> is as defined previously is formed using the same procedure as for compound (XI).

When R<sub>2</sub>=Me and X=I, this starting material (IV) could synthetized with the following scheme c.

Scheme c

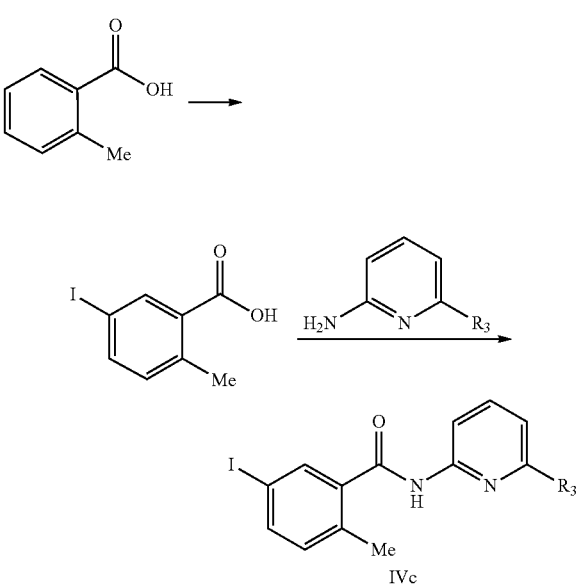

IVc

The iodination of 2-methyl benzoic acid is achieved using for instance N-iodosuccinimide or iodine in concentrated sulfuric acid at temperature from 0° C. to room temperature to give 5-iodo-2-methylbenzoic acid.

The next step is performed using the same procedure as for compound (IV).

The second synthetic approach for obtaining compounds of Formula (I) and/or on salified form (II) thereof is depicted in the following Scheme 4.

Scheme 4
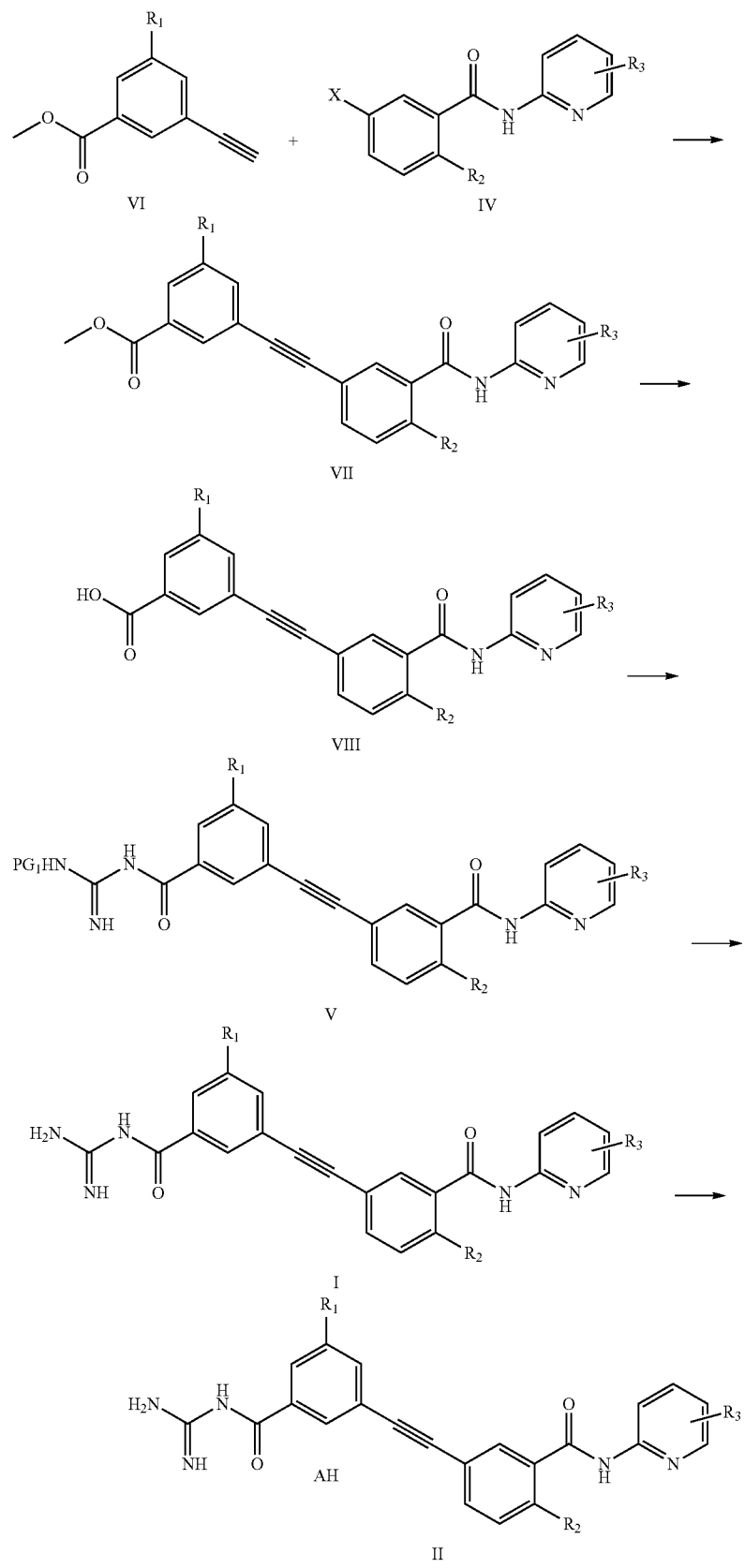

Thus, the present disclosure is also directed to another process for the preparation of a compound of formula (I) or a pharmaceutically acceptable salt thereof comprising at least the following steps consisting in:

(1) performing a catalytic coupling, in particular with a Palladium catalyst, between an intermediate compounds of formula (IV)

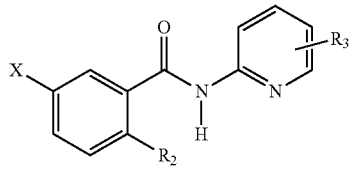
(IV)

wherein $R_2$ and $R_3$ are as defined in formula (I) and

X is a bromine atom or an iodine atom, and an intermediate compound of formula (VI)

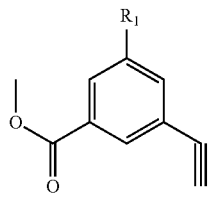
(VI)

wherein:

$R_1$ means a fluorine atom or a perhalogeno linear alkyl radical containing 1, 2 or 3 carbon atoms such as a trifluoromethyl radical;

so as to obtain a compound of formula (VII)

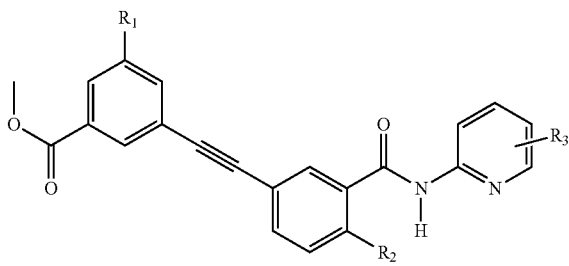
(VII)

wherein $R_1$, $R_2$, and $R_3$ are as defined above;

(2) having said compound of formula (VII) in contact with a base such as lithium hydroxide or sodium hydroxide to obtain a compound of formula (VIII)

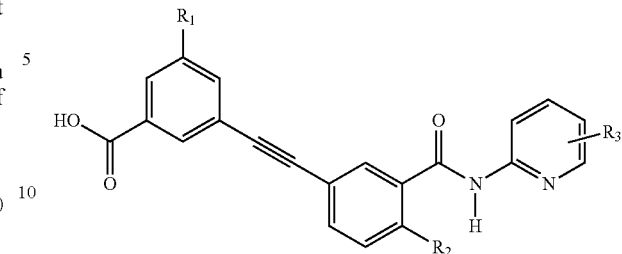
(VIII)

wherein $R_1$, $R_2$, and $R_3$ are as defined above;

(3) contacting the so-obtained compound of formula (VIII) of step (2) with at least one amide formation reagent such as dicyclohexylcarbodiimide or benzotriazol-1-yloxytripyrrolidinophosphonium hexafluorophosphate, and pentafluorophenol in presence of $PG_1$ guanidine such as N-Boc guanidine or N-Cbz guanidine to obtain a compound of formula (V)

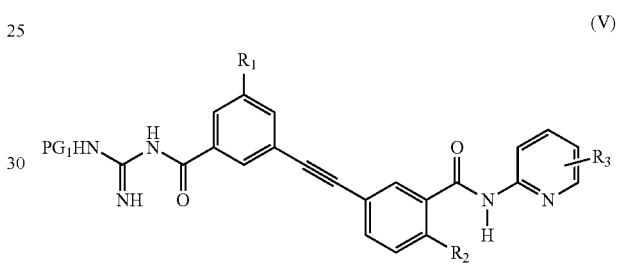
(V)

wherein $R_1$, $R_2$, $R_3$ and $PG_1$ are as defined above;

said compound of formula (V) being further deprotected and optionally salified to obtain the expected compound of formula (I) or a pharmaceutically acceptable salt thereof.

According to this second route, different starting materials are considered for performing the intermediate product (V) wherein $R_2$ and $R_3$ are as defined previously and X means an iodine atom or a bromine atom. More particularly, the compound (IV) wherein $R_1$ is as defined previously is in this case coupled with the compound (VI) with similar conditions to these detailed in respect to the scheme 1.

Then, a base such as lithium hydroxide or sodium hydroxide may be added to an ice cooled solution of the intermediate compound (VII) in an aqueous organic solvent, and the mixture may be kept under stirring at room temperature for 3 hours. The reaction mixture may be then concentrated and acidified for precipitating the compound (VIII). The compound (III) may be recovered and purified before the following step.

Further, a solution of said compound (III) with amide formation reagents such as dicyclohexylcarbodiimide or benzotriazol-1-yl-oxytripyrrolidinophosphonium hexafluorophosphate and pentafluorophenol may be stirred at room temperature for 3 hours in a solvent such as tetrahydrofuran or dimethylformamide. After the completion of the reaction, and removing of the precipitates by for example filtration, the filtrate may be recovered and purified to recover the compound (V) under a solid material.

The compound (V) may be then solubilized in a solvent like tetrahydrofuran or dichloromethane in presence of $PG_1$ guanidine such as N-Boc guanidine or N-Cbz guanidine and stirred at room temperature. After completion of reaction, the expected compound (I) is recovered. As disclosed in previous scheme 1, other compounds of formula (I), like compounds of formula (II), that correspond to salified forms of compounds (I) may be synthetized therefrom Both methods respectively detailed in schemes 1 and 4 may advantageously also comprise subsequent steps of purifying and/or isolating intermediate or final products obtained. Convenient methods of purification are detailed in the following examples. In particular, the purification of compounds may be performed by preparative high-performance liquid chromatography (HPLC).

The instant disclosure will be better understood from the examples that follow, all of which are intended for illustrative purposes only and are not meant to limit the scope of the instant disclosure in any way.

The examples that follow illustrate the preparation of certain compounds in accordance with the invention, without, however, limiting it. The numbers of the illustrated compounds refer to those given in Table 1 above, which illustrates the chemical structures and physical properties of a number of compounds according to the invention.

EXAMPLES—COMPOUNDS

Materials and Methods $^1$H NMR and $^{13}$C NMR data were recorded on Bruker 400 MHz AVANCE series or Bruker 300 MHz DPX Spectrometer with CDCl$_3$ or DMSO-d$_6$ or CD$_3$OD as solvent. $^1$H chemical shifts were referenced at 7.26 ppm for CDCl$_3$, 2.5 ppm for DMSO-d$_6$ and 3.3 ppm for CD$_3$OD. $^{13}$C chemical shifts were referenced at 77 ppm for CDCl$_3$, 39 ppm for DMSO-d$_6$ and 44 ppm for CD$_3$OD, and obtained with $^1$H decoupling. Multiplicities are abbreviated as follows: singlet (s), doublet (d), triplet (t), quartet (q), doublet-doublet (dd), quintet (quint), sextet (sextet), septet (septet), multiplet (m), and broad (br).

MS was measured on Agilent 1200/1260 Series LC/MSD mass spectrometer. Column: Zorbax XDB C18 (50×4.6) mm, 5 μm or Acquity BEH C18 (50×2.1 mm; 1.7 μm). Mobile phase: Solvent A: 0.1% Formic Acid in Milli-Q water (or) 0.1% Trifluoroacetic acid in Milli-Q-water. Solvent B: Acetonitrile. Flow rate: 1.5 mL/min. Injection Volume: 2 μL. Wave length: Maximum chromatogram (210-400 nm). Run time: 6.0 min. Ionization source: Multi-mode (ESI and APCI).

Purity was measured on Agilent 1200/1260 Series HPLC spectrometer. Column: C18 (250×4.6) mm, 5 μm (or) C18 (150×4.6) mm, 5 μm. Mobile phase: Solvent A: 10 mM ammonium acetate in Milli-Q water (or) 0.1% Trifluoroacetic acid in Milli-Q-water. Solvent B: Acetonitrile. Flow rate: 1.0 mL/min. Injection Volume: 2 μL. Wave length: Maximum chromatogram (210-400 nm). Run time: 30 min.

For compound 1c, MS was measured with UPLC-SQD (Simple Quad, from Waters). Column: Acquity BEH C18 (50×2.1 mm; 1.7 μm). Mobile phase: solvent A: H$_2$O+0.05% TFA solvent B: CH$_3$CN+0.035% TFA. Flow rate; 1 mL/min. UV Detection: I=220 nm. MS Detection (Simple Quad) Ionization: ESI+Electrospray First/Last Mass (uma) FS: 160/1200 uma Capillary voltage (KV): 3.5. Cone (V): 20. Source Temperature (° C.): 150. Desolvation temperature (° C.): 500. Desolvation gas flow (L/hr): 1200. Cone gas flow (L/hr): 100. LM 1 resolution: 13.00. HM1 resolution: 13.00. Ion energy 1:0.20.

For the compound obtained at the end of step 1 in the preparation of Intermediate 2, LC-MS was measured by the following Method: Column: XBridge C18, 4.6*50 mm, 3.5 μm Mobile phase: H$_2$O (10 mmol NH$_4$HCO$_3$) (A)/ACN(B) Elution program: Gradient from 5 to 95% of B in 1.6 min at 1.8 ml/min Temperature: 50° C. Detection: UV (214, 4 nm) and MS (ESI, Pos mode, 110 to 1000 amu).

The reactions requiring anhydrous conditions were performed under an inert atmosphere (nitrogen or argon) with anhydrous solvents (with or without molecular sieves).

All R$_1$, R$_2$, R$_3$ in the following schemes are as defined above when not specified.

Example 1

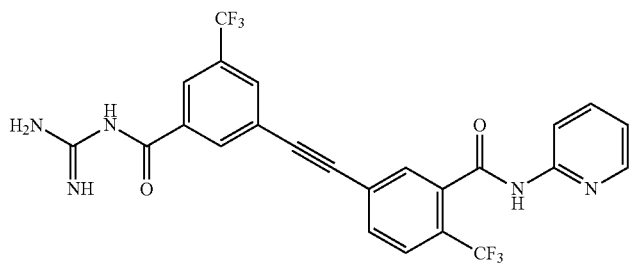

compound 1a: as free base
compound 1b: as hydrochloride salt
compound 1c: as malonate salt

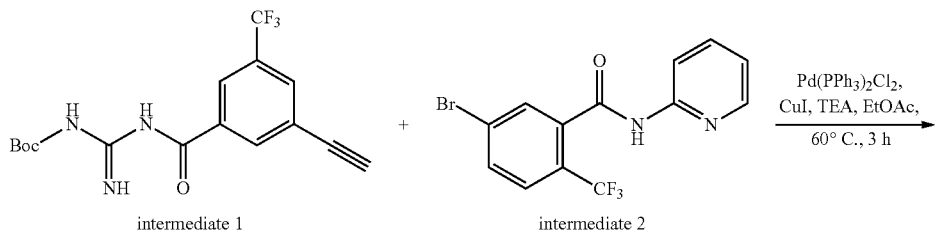

intermediate 1      intermediate 2

-continued

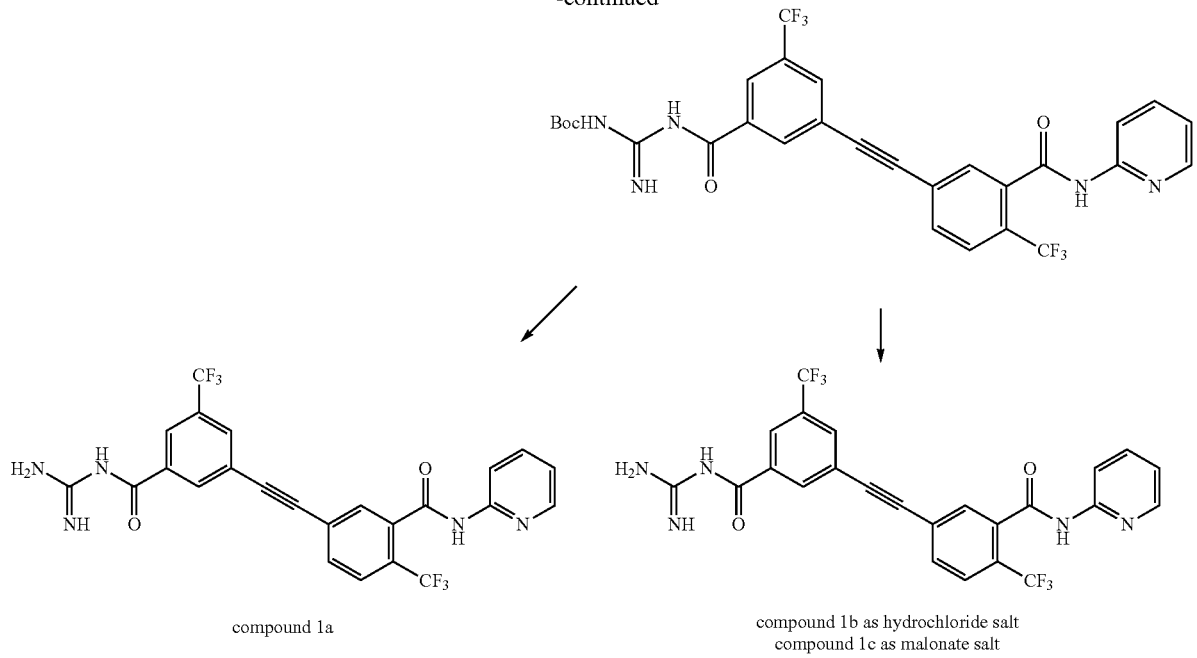

compound 1a compound 1b as hydrochloride salt
compound 1c as malonate salt

Compound 1a (as Base)

Step 1: To a degassed solution of 5-Bromo-N-pyridin-2-yl-2-trifluoromethyl-benzamide intermediate 2 (25.0 g, 72.46 mmol) and tert-butyl N—[N-[3-ethynyl-5-(trifluoromethyl)benzoyl]carbamimidoyl]carbamate intermediate 1 (28.29 g, 79.71 mmol) in dry ethyl acetate (250 mL) in a sealed tube were added cuprous iodide (0.68 g, 3.62 mmol), triethyl amine (31.41 mL, 217.35 mmol) and bis(triphenylphosphine)palladium(II) dichloride (5.08 g, 7.24 mmol). The reaction mixture was degassed again for 10 min and heated at 65° C. for 4 hours. The completion of reaction was observed by TLC. The reaction mixture was cooled to room temperature, diluted with ethyl acetate and filtered through celite bed. The filtrate was concentrated in vacuum and was purified through silica gel (230-400 mesh) column chromatography using ethyl acetate in petroleum ether to afford tert-butyl N—[N-[3-[2-[3-(2-pyridylcarbamoyl)-4-(trifluoromethyl)phenyl]ethynyl]-5-(trifluoromethyl)benzoyl]carbamimidoyl]carbamate (18.0 g, 40%) as off white solid.

Step 2: To an ice cooled solution of tert-butyl N—[N-[3-[2-[3-(2-pyridylcarbamoyl)-4-(trifluoromethyl)phenyl]ethynyl]-5-(trifluoromethyl)benzoyl]carbamimidoyl]carbamate (18.0 g, 29.07 mmol) in dry dichloromethane (150 mL) was added trifluoroacetic acid (66.3 g, 581.58 mmol) and stirred at room temperature for 12 hours. The completion of reaction was observed by TLC. The reaction mixture was evaporated under reduced pressure. The crude material was triturated with diethyl ether and the solid formed was filtered to afford the salt as off white solid. This was mixed with ice and basified using 10% $NaHCO_3$ solution. The solid formed was filtered, washed with water, hexane and dried under vacuum to afford 5-((3-(carbamimidoylcarbamoyl)-5-(trifluoromethyl)phenyl)ethynyl)-N-(pyridin-2-yl)-2-(trifluoromethyl)benzamide compound 1a (14.6 g, 96%) as white solid.

LC-MS APCI: Calculated for $C_{24}H_{15}F_6N_5O_2$ 519.41; Observed m/z $[M+H]^+$520.41.

Purity by LC-MS: 98.04%. RT: 3.09.
Purity by HPLC: 99.38%. RT: 12.79.
$^1$HNMR (400 MHz, DMSO-$d_6$): δ 11.21 (s, 1H), 8.52 (s, 1H), 8.38-8.40 (m, 2H), 8.17 (d, J=8.00 Hz, 1H), 8.11 (s, 2H), 7.99 (s, 1H), 7.86-7.92 (m, 3H), 7.20 (t, J=6.40 Hz, 1H), 6.88 (bs, 2H).

Compound 1b (as Hydrochloride Salt)

Step 1: To a degassed solution of 5-Bromo-N-pyridin-2-yl-2-trifluoromethyl-benzamide intermediate 2 (9.0 g, 26.09 mmol) and tert-butyl N—[N-[3-ethynyl-5-(trifluoromethyl)benzoyl]carbamimidoyl]carbamate intermediate 1 (11.11 g, 31.30 mmol) in dry ethyl acetate (100 mL) in a sealed tube were added cuprous iodide (0.25 g, 1.30 mmol), triethyl amine (10.90 mL, 78.26 mmol) and bis(triphenylphosphine) palladium(II) dichloride (1.83 g, 2.61 mmol). The reaction mixture was degassed again for 10 min and heated at 65° C. for 5 hours. The completion of reaction was observed by TLC. The reaction mixture was allowed to room temperature and diluted with ethyl acetate and filtered through celite bed. The filtrate was concentrated in vacuum and was purified through silica gel (230-400 mesh) column chromatography using ethyl acetate in petroleum ether to afford tert-butyl N—[N-[3-[2-[3-(2-pyridylcarbamoyl)-4-(trifluoromethyl) phenyl]ethynyl]-5-(trifluoromethyl)benzoyl]carbamimidoyl]carbamate (8.5 g, 53%) as yellow solid.

Step 2: Concentrated. HCl (200 mL) was slowly added to tert-butyl N—[N-[3-[2-[3-(2-pyridylcarbamoyl)-4-(trifluoromethyl)phenyl]ethynyl]-5-(trifluoromethyl)benzoyl]carbamimidoyl]carbamate (8.5 g, 13.73 mmol) with ice cooling. The resulting suspension was stirred at room temperature for 6 hours. The precipitated solid was filtered, washed with water and dried. This material was further dried using lyophilizer for 36 hours to yield 5-(3-(carbamimidoyl)carbamoyl)-5-(trifluoromethyl)phenyl)ethynyl)-N-(pyridin-2-yl)-2-(trifluoromethyl)benzamide hydrochloride compound 1b (6.1 g, 80%) as off white solid.

¹H NMR (400 MHz, DMSO-d6): 12.39 (s, 1H), 11.29 (s, 1H), 8.66 (s, 4H), 8.61 (s, 1H), 8.50 (s, 1H), 8.38 (s, 2H), 8.15 (d, J=8.00 Hz, 1H), 8.00 (s, 1H), 7.88-7.96 (m, 3H), 7.20-7.88 (m, 1H)

LC-MS APCI: Calculated for $C_{24}H_{15}F_6N_5O_2$ 519.41; Observed m/z $[M+H]^+$520.41.

Purity by LC-MS: 99.81%. RT: 2.55.
Purity by HPLC: 98.57%. RT: 11.99.

Compound 1c (as Malonate Salt)

Step 1: In a reactor under nitrogen are charged 5-Bromo-N-pyridin-2-yl-2-trifluoromethyl-benzamide intermediate 2 (0.690 kg, 2 mol., 1 eq), cuprous iodide (0.019 kg, 0.1 mol., 0.05 eq), $Pd(PPh_3)_2Cl_2$ (0.140 kg, 0.2 mol., 0.1 eq) and acetonitrile (6.6 L, 9.5 vol). The tert-butyl N—[N-[3-ethynyl-5-(trifluoromethyl)benzoyl] carbamimidoyl]carbamate compound intermediate 1 (0.924 kg, 2.6 mol., 1.3 eq) was added in 5 min on the suspension under stirring at 25° C. This addition is slightly endothermic. The suspension was degassed under nitrogen bubbling during 30 min under stirring. Then triethylamine (0.605 kg, 5.98 mol., 3 eq) was added in 17 min at 25° C. mass. An exotherm of +6° C. is observed. The dropping funnel was washed with acetonitrile (0.5 L, 0.7 vol). The reaction mixture was heated at 45° C. and maintained for 2 hours until less than 1% (that is to say until less than 9.24 g, until less than 0.026 mole) of intermediate 1 is present. The suspension was then cooled to 10° C. (at −20° C./hour) and maintained for 1 hour. The intermediate tert-butyl N—[N-[3-[2-[3-(2-pyridylcarbamoyl)-4-(trifluoromethyl)phenyl]ethynyl]-5-(trifluoromethyl)benzoyl]carbamimidoyl]carbamate was filtered and the cake was washed with acetonitrile (1.4 L, 2 vol) then with water (0.7 L, 1 vol). After drying by nitrogen flux (1 night, 0.3 bar) 0.745 kg of tert-butyl N—[N-[3-[2-[3-(2-pyridylcarbamoyl)-4-(trifluoromethyl)phenyl]ethynyl]-5-(trifluoromethyl)benzoyl]carbamimidoyl]carbamate was isolated with a yield of 60%.

Step 2: A suspension of tert-butyl N—[N-[3-[2-[3-(2-pyridylcarbamoyl)-4-(trifluoromethyl)phenyl]ethynyl]-5-trifluoromethyl)benzoyl]carbamimidoyl]carbamate (1.5 kg, 2.42 mol) in ethyl acetate (14.5 L) was heated at 70° C. under stirring. Trifluoroacetic acid (2.2 kg, 8 eq) was added in 30 min at 70° C. The dropping funnel was washed with ethyl acetate (0.75 L, 0.5 vol). The reaction mixture was maintained 22 hours at 70° C. until less than 1% (that is to say until less than 15 g, until less than 0.0242 mol) of tert-butyl N—[N-[3-[2-[3-(2-pyridylcarbamoyl)-4-(trifluoromethyl)phenyl]ethynyl]-5-trifluoromethyl)benzoyl]carbamimidoyl]carbamate. After cooling at 20° C. the mixture was basified by addition of a solution of NH4OH 28% in 1 hour until pH=9-10. After an additional 15 min stirring, water (11.3 L, 7.5 vol) was added. The phases were separated. The organic layer was diluted with ethyl acetate (45 L, 30 vol) and washed successively with an aqueous solution of sodium metabisulfite ($Na_2S_2O_5$ 0.15 kg in 15 L water) and water (15 L, 10 vol). An additional treatment with charcoal (Darco S51) was realized. The ethyl acetate solution (56.37 kg) was engaged in the next salification step.

A part of the previous solution of 5-((3-(carbamimidoyl-carbamoyl)-5-(trifluoromethyl)phenyl)ethynyl)-N-(pyridin-2-yl)-2-(trifluoromethyl)benzamide estimated pure 0.958 kg, 1.844 mol, 1 eq) was concentrated under reduce pressure (100 mbars, 50° C.) until 10 volumes of ethyl acetate. An additional azeotropic drying was realized with 15 vol ethyl acetate. The obtained 10 vol solution was heated at 50° C., and then a seeding with 2% of 5-((3-(carbamimidoylcarbamoyl)-5-(trifluoromethyl)phenyl)ethynyl)-N-(pyridin-2-yl)-2-(trifluoromethyl)benzamide malonic acid was done. A solution of malonic acid (0.192 kg, 1.144 mol, 1 eq) in ethyl acetate (2.8 L, 2.9 vol) was added in 30 min at 50° C. The dropping funnel is washed with 0.4 L of ethyl acetate. The crystallization was observed during the acid addition. Stirring was maintained for 1 hour at 50° C. and cooled at 10° C. (−20° C./hour). 5-((3-(carbamimidoylcarbamoyl)-5-(trifluoromethyl)phenyl)ethynyl)-N-(pyridin-2-yl)-2-(trifluoromethyl)benzamide malonic acid was isolated by a fast filtration and the cake was washed twice with 1 L ethyl acetate. The product was dried under nitrogen flux during 1 night to offer 1.096 kg of 5-((3-(carbamimidoylcarbamoyl)-5-(trifluoromethyl)phenyl)ethynyl)-N-(pyridin-2-yl)-2-(trifluoromethyl)benzamide malonic acid compound 1c with a yield of 95.3%.

¹H NMR (400 MHz, DMSO-d6): 12.82 (bs, 1H), 11.19 (s, 1H), 8.51 (s, 1H), 8.39 (s, 1H), 8.38 (m, 1H), 8.17 (d, J=10.3 Hz, 1H), 8.12 (s, 1H), 7.98 (s, 1H), 7.91 (s, 2H), 7.87 (ddd, J=8.0, 7.8.

LC-MS APCI: Calculated for $C_{24}H_{15}F_6N_5O_2$ 519.41; Observed m/z $[M+H]^+$520.02.

Purity by LC-MS: 99.1%. RT: 2.67.
Purity by HPLC: 98.5%. RT: 9.57.

INTERMEDIATE 1

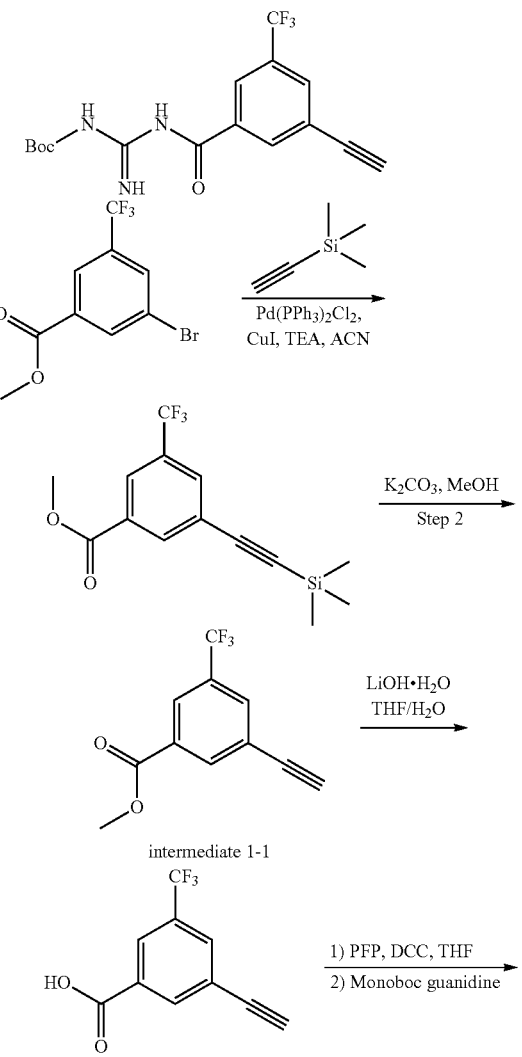

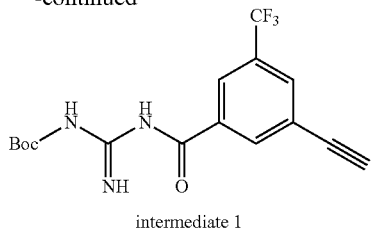

intermediate 1

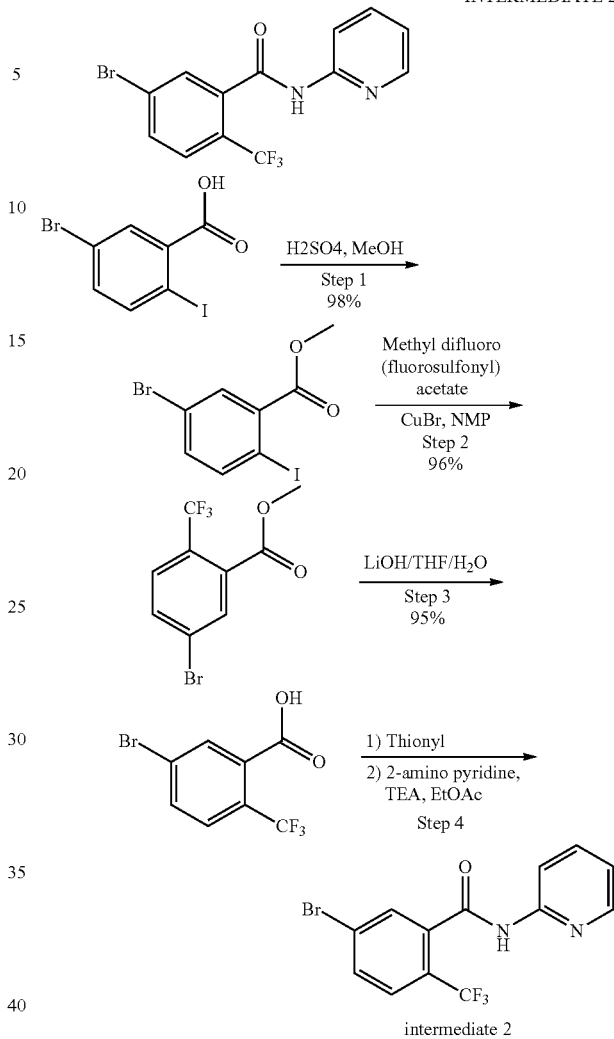

intermediate 2

Step 1: To a degassed solution of methyl 3-bromo-5-(trifluoromethyl)benzoate (20.0 g, 70.67 mmol) and trimethylsilylacetylene (17.4 g, 176.67 mmol) in acetonitrile (100 mL) in a sealed tube was added Pd(PPh$_3$)$_2$Cl$_2$ (4.96 g, 7.07 mmol) and cuprous iodide (1.34 g, 7.06 mmol). The tube was degassed again and heated at 70° C. for 2 hours. The reaction mixture was cooled and filtered through celite bed. The filtrate was concentrated in vacuum and the residue purified through silica gel (60-120 mesh) column chromatography using petroleum ether to afford 3-Trifluoromethyl-5-trimethylsilanylethynyl-benzoic acid methyl ester (14 g, 66%) as yellow liquid.

Step 2: To a solution of 3-Trifluoromethyl-5-trimethylsilanylethynyl-benzoic acid methyl ester (14.0 g, 46.60 mmol) in methanol (50 mL) was added potassium carbonate (0.58 g, 4.2 mmol) and stirred at room temperature for 20 minutes. The reaction mixture was concentrated under reduced pressure. The residue was diluted with ethyl acetate (100 mL), washed with water, brine, dried over anhydrous sodium sulphate and concentrated to yield 3-Ethynyl-5-trifluoromethyl-benzoic acid methyl ester intermediate 1-1 (11 g, 61%) as a brown liquid.

Step 3: To an ice cooled solution of 3-Ethynyl-5-trifluoromethyl-benzoic acid methyl ester (11.0 g, 48.03 mmol) in tetrahydrofuran (50 mL) and water (25 mL) was added lithium hydroxide (6.0 g, 144.10 mmol) and stirred at room temperature for 3 hours. The reaction mixture was concentrated and acidified with aqueous citric acid solution. The precipitated solid was filtered, washed with water and dried to afford 3-Ethynyl-5-trifluoromethyl-benzoic acid (9.2 g, 78%) as pale brown solid.

Step 4: To a solution of 3-Ethynyl-5-trifluoromethyl-benzoic acid (9.2 g, 42.99 mmol), dicyclohexylcarbodiimide (13.28 g, 64.48 mmol) and pentafluorophenol (11.8 g, 64.48 mmol) in tetrahydrofuran (50 mL) was stirred at room temperature for 3 hours. After the completion of the reaction, the mixture was cooled using ice bath and the precipitated dicyclohexylurea was removed by filtration. The filtrate was concentrated and purified by silica gel (60-120 mesh) column chromatography using ethyl acetate in petroleum ether to provide the 3-Ethynyl-5-trifluoromethyl-benzoic acid pentafluorophenyl ester (13.6 g, 83%) as an off white solid.

Step 5: To a solution of 3-Ethynyl-5-trifluoromethyl-benzoic acid pentafluorophenyl ester (13.6 g, 35.78 mmol) in tetrahydrofuran was added monobocguanidine (6.82 g, 42.94 mmol) and stirred at room temperature for 4 hours. After completion of reaction, the reaction mixture was evaporated and was purified through silica gel (60-120 mesh) column chromatography using ethyl acetate in petroleum ether to afford tert-butyl N—[N-[3-ethynyl-5-(trifluoromethyl)benzoyl]carbamimidoyl]carbamate intermediate 1 (8.2 g, 64%) as an off white solid.

Step 1: Concentrated H$_2$SO$_4$ (10 mL) was added dropwise to the solution of 5-bromo-2-iodobenzoic acid (100 g, 305.89 mmol) in MeOH (800 mL). The mixture was refluxed for 16 hours and then concentrated. The residue was dissolved in ethyl acetate (1 L). The organic layer was washed with saturated NaHCO$_3$ and brine (3×200 mL), dried over Na$_2$SO4, filtered and concentrated to afford target product 5-Bromo-2-iodo-benzoic acid methyl ester (101.4 g, yield 90%) as yellow solid.

LC purity: 98.91% (254 nm); Mass: find peak 341 (M+H)+ at 2.214 min.

Step 2: To a solution of 5-Bromo-2-iodo-benzoic acid methyl ester (24 g, 70.4 mmol) and methyl 2,2-difluoro-2-(fluorosulfonyl)acetate (13.5 mL, 105.6 mmol) in N-methyl-2-pyrrolidinone (80 mL) was added copper (I) bromide (1.21 g, 8.45 mmol). The reaction mixture was stirred at 100° C. for 5 hours. The reaction was filtered and partitioned between ethyl acetate and brine. The aqueous layer was extracted with ethyl acetate, and the organic layers were combined and dried over Na2SO4. After filtration, the solvent was removed in vacuo. The residue was purified by silica gel column (0-4% Ethyl acetate in Petroleum ether) to give the 5-Bromo-2-trifluoromethyl-benzoic acid methyl ester (1 19.2 g, yield 96%) as yellow oil.

Step 3: To an ice cooled solution of 5-Bromo-2-trifluoromethyl-benzoic acid methyl ester (9.1 g, 35.68 mmol) in tetrahydrofuran (20 mL) and water (10 mL) was added lithium hydroxide (4.4 g, 104.76 mmol) and stirred at room temperature for 3 hours. The reaction mixture was concentrated and acidified with aqueous citric acid solution. The precipitated solid was filtered, washed with water and dried to afford 5-Bromo-2-trifluoromethyl-benzoic acid (8 g, 95%) as pale yellow solid.

Step 4: A solution of 5-Bromo-2-trifluoromethyl-benzoic acid (8.0 g, 29.74 mmol) in thionyl chloride (40 mL) was heated to reflux for 3 hours. The completion of reaction was observed by TLC (by converting acid chloride to methyl ester). The thionyl chloride was evaporated and the residue was charged to the reaction mixture contained 2-amino pyridine (3.2 g, 32.71 mmol), triethyl amine (12.44 mL, 89.21 mmol) in dry ethyl acetate (80 mL) at 0° C. The reaction mixture was stirred at RT (room temperature) for 12 hours. The completion of reaction was observed by TLC. The reaction mixture was taken in water (200 mL), extracted with ethyl acetate (2×200 mL). The combined organic layer was washed with water (2×100 mL), brine, dried over sodium sulphate and evaporated. The crude material was purified by column chromatography using ethyl acetate in petroleum ether to afford 5-Bromo-N-pyridin-2-yl-2-trifluoromethyl-benzamide Intermediate 2 (5.1 g, 49%) as off white solid.

Example 2

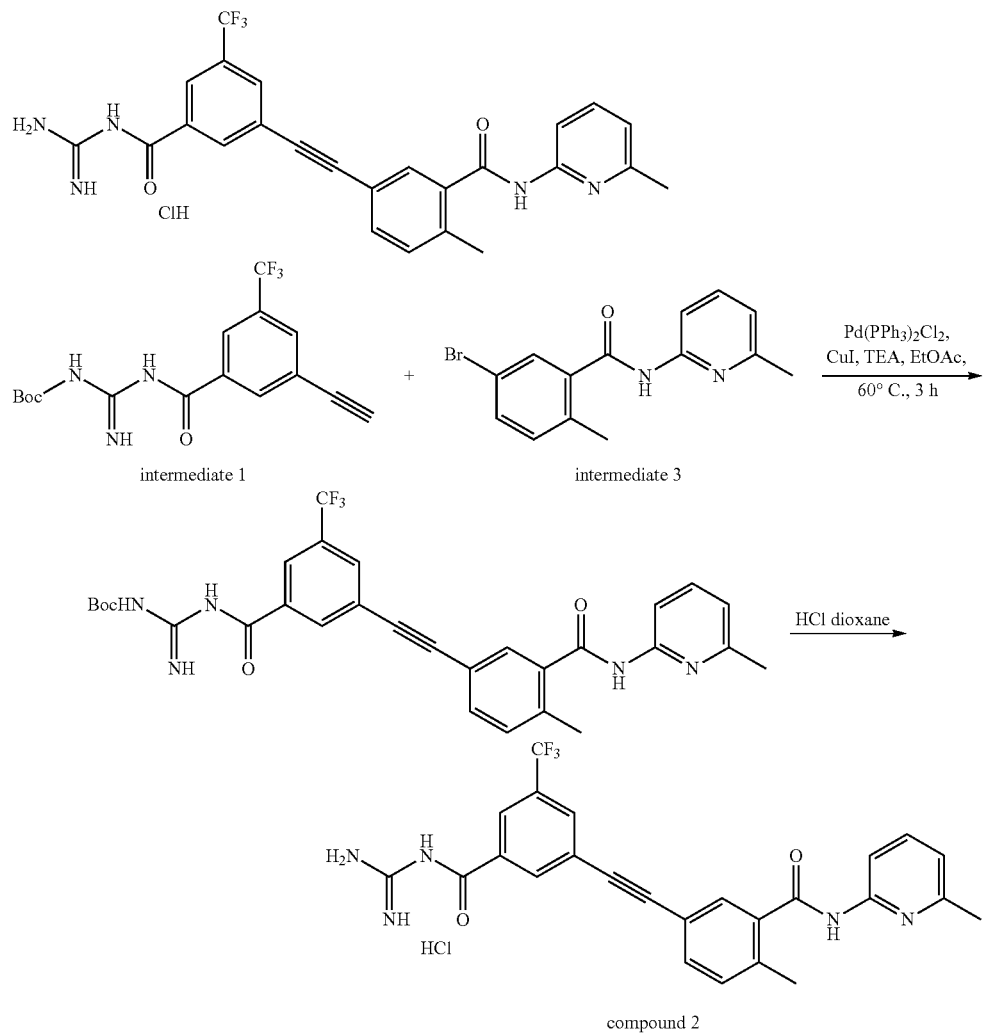

compound 2

Step 1: To a degassed solution of tert-butyl N—[N-[3-ethynyl-5-(trifluoromethyl)benzoyl]carbamimidoyl]carbamate intermediate 1 (1.5 g, 4.22 mmol) and 5-bromo-2-methyl-N-(6-methylpyridin-2-yl)benzamide intermediate 3 (0.89 g, 2.92 mmol) in dry ethyl acetate (20 mL) in a round bottom flask were added cuprous iodide (0.04 g, 0.211 mmol), triethyl amine (1.42 g, 14.08 mmol) and bis(triphenylphosphine)palladium(II) dichloride (0.3 g, 0.42 mmol). The reaction mixture was degassed again for 10 min and heated at 60° C. for 3 hours. The completion of reaction was observed by TLC. The reaction mixture was cooled, diluted with ethyl acetate and filtered through celite bed. The filtrate was concentrated under vacuum and the crude material was purified through silica gel (230-400 mesh) column chromatography using ethyl acetate in petroleum ether to afford 5-[2-[3-(carbamimidoylcarbamoyl)-5-(trifluoromethyl)phenyl]ethynyl]-2-methyl-N-(2-pyridyl)benzamide (0.93 g, 37%) as pale brown solid.

Step 2: To an ice cooled solution of 5-[2-[3-(carbamimidoylcarbamoyl)-5-(trifluoromethyl)phenyl]ethynyl]-2-methyl-N-(2-pyridyl)benzamide (0.93 g, 1.60 mmol) in HCl in dioxane (10 mL) and stirred for 12 hours. The reaction mixture was filtered, the solid was washed with hexane and dried under vacuum. The product was further purified by Preparative HPLC method. The obtained solid was stirred with HCl in diethyl ether for 1 hour to afford 5-((3-(((diaminomethylene)carbamoyl)-5-(trifluoromethyl)phenyl)ethynyl)-2-methyl-N-(6-methylpyridin-2-yl)benzamide hydrochloride compound 2 (0.075 g, 9%) as off white solid.

$^1$H-NMR (400 MHz, DMSO-d6): δ 12.38 (s, 1H), 11.03 (s, 1H), 8.67 (m, 4H), 8.54 (s, 1H), 8.45 (s, 1H), 8.00 (d, J=8.00 Hz, 1H), 7.83 (t, J=8.00 Hz, 1H), 7.62 (s, 1H), 7.63 (d, J=7.60 Hz, 1H), 7.40 (d, J=8.00 Hz, 1H), 7.11 (d, J=7.60 Hz, 1H), 2.46 (s, 3H), 2.46 (s, 3H).

LC-MS APCI: Calculated for $C_{25}H_{20}F_3N_5O_2$ 479.46; Observed m/z [M+H]+480.4.

Purity by LC-MS: 99.38%.
Purity by HPLC: 98.64%.

INTERMEDIATE 3

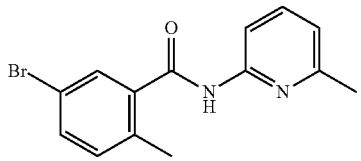

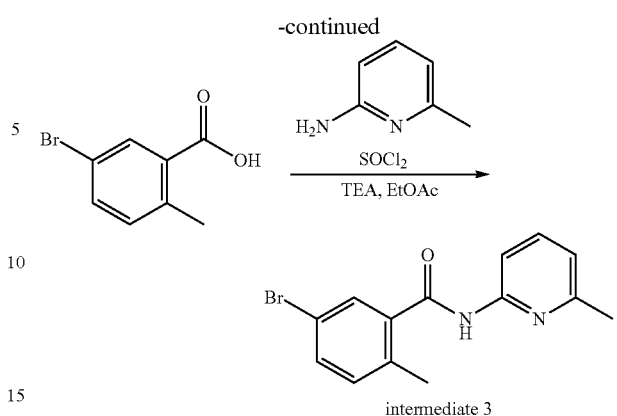

intermediate 3

A solution of 5-bromo-2-methylbenzoic acid (5.0 g, 23.25 mmol) in thionyl chloride (15 mL) was heated at reflux for 3 hours. The completion of reaction was observed by TLC. The thionyl chloride was evaporated and the residue was charged to the reaction mixture contained 6-methylpyridin-2-amine (2.5 g, 23.14 mmol), triethyl amine (5.8 g, 57.34 mmol) in dry ethyl acetate (50 mL) at 0° C. The reaction mixture was stirred at RT (room temperature) for 12 hours. The completion of reaction was observed by TLC. The reaction mixture was taken in water (200 mL), extracted with ethyl acetate (2×100 mL). The combined organic layer was washed with water (2×100 mL), brine, dried over sodium sulphate and evaporated. The crude was purified by column chromatography using ethyl acetate in petroleum ether to afford 5-bromo-2-methyl-N-(6-methyl-2-pyridyl)benzamide intermediate 3 (4 g, 57%) as an off white solid.

Example 3

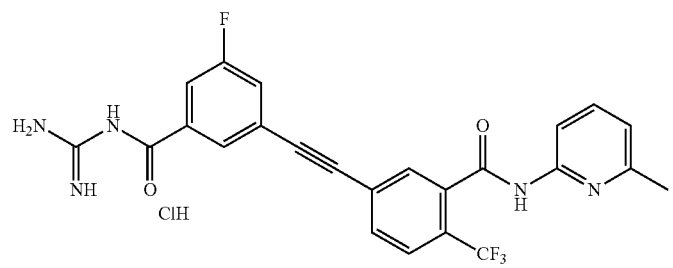

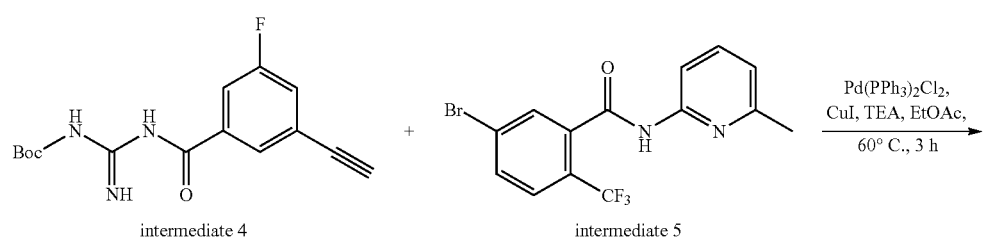

intermediate 4      intermediate 5

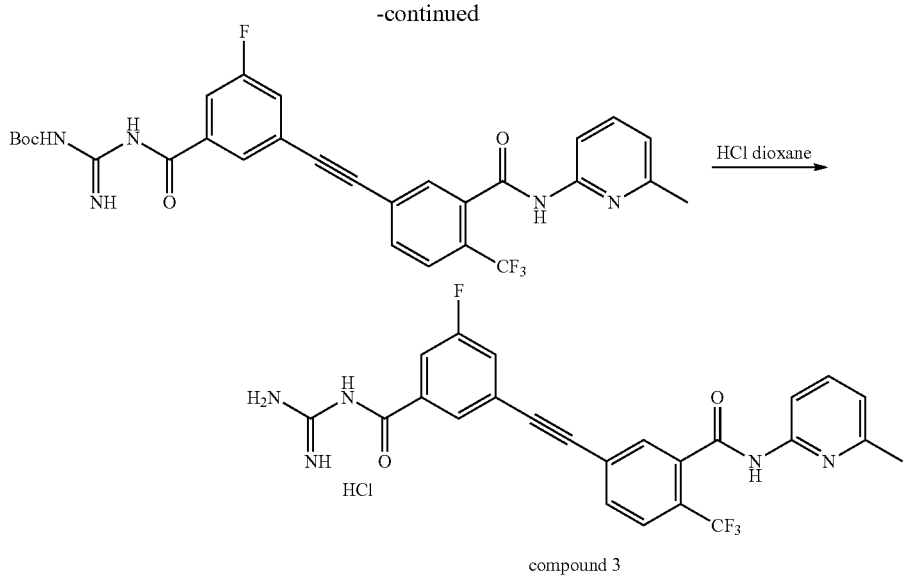

compound 3

Step 1: To a degassed solution of tert-butyl N—[N-(3-ethynyl-5-fluoro-benzoyl)carbamimidoyl]carbamate intermediate 4 (2 g, 6.55 mmol) and 5-bromo-N-(6-methylpyridin-2-yl)-2-(trifluoromethyl)benzamide intermediate 5 (1.6 g, 4.45 mmol) in dry ethyl acetate (15 mL) in a round bottom flask were added cuprous iodide (0.05 g, 0.26 mmol), triethyl amine (1.4 g, 13.83 mmol) and bis(triphenylphosphine)palladium(II) dichloride (0.46 g, 0.65 mmol). The reaction mixture was degassed again for 10 min and heated at 60° C. for 3 hours. The completion of reaction was observed by TLC. The reaction mixture was cooled, diluted with ethyl acetate and filtered through celite bed. The filtrate was concentrated under vacuum and the crude material was purified through silica gel (230-400 mesh) column chromatography using ethyl acetate in petroleum ether to afford tert-butyl N—[N-[3-fluoro-5-[2-[3-[(6-methyl-2-pyridyl)carbamoyl]-4-(trifluoromethyl)phenyl]ethynyl]benzoyl]carbamimidoyl]carbamate (0.8 g, 21%) as yellow solid.

Step 2: To an ice cooled solution of tert-butyl N—[N-[3-fluoro-5-[2-[3-[(6-methyl-2-pyridyl)carbamoyl]-4-(trifluoromethyl)phenyl]ethynyl]benzoyl]carbamimidoyl]carbamate (0.8 g, 1.37 mmol) in dioxane was added HCl in dioxane (10 mL) and stirred for 4 hours. The reaction mixture was filtered, the solid was washed with hexane and dried under vacuum. The product was further purified by Preparative HPLC method. The obtained solid was stirred with HCl in diethyl ether for 1 hour to afford 5-((3-(carbamimidoylcarbamoyl)-5-fluorophenyl)ethynyl)-N-(6-methylpyridin-2-yl)-2-(trifluoromethyl)benzamide hydrochloride compound 3 (0.14 g, 25%) as off white solid.

$^1$H-NMR (400 MHz, DMSO-d6): δ 12.31 (s, 1H), 11.21 (s, 1H), 8.67-8.72 (m, 4H), 8.22 (s, 1H), 8.11 (dd, J=1.60, 9.20 Hz, 1H), 7.86-7.97 (m, 5H), 7.76-7.79 (m, 1H), 7.08 (d, J=7.20 Hz, 1H), 2.43 (s, 3H).

LC-MS APCI: Calculated for $C_{24}H_{17}F_4N_5O_2$ 483.43; Observed m/z [M+H] 484.0.

Purity by LC-MS: 98.13%.
Purity by HPLC: 98.62%.

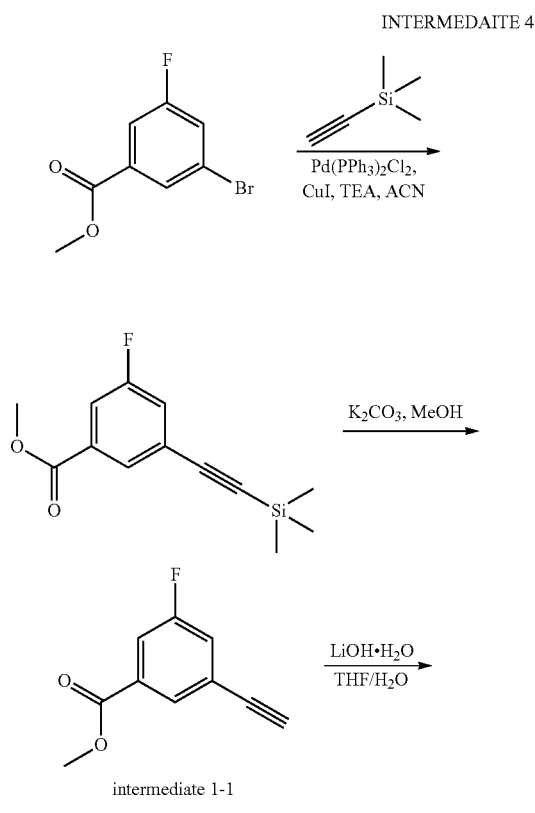

INTERMEDIATE 4 intermediate 1-1

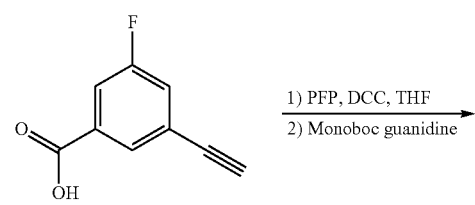

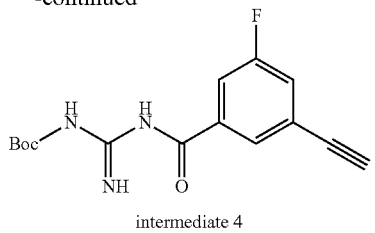

intermediate 4

Step 1: To a degassed solution of methyl 3-bromo-5-fluorobenzoate (14 g, 60.0 mmol) and trimethyl silyl acetylene (14.7 g, 150.21 mmol) and triethyl amine (14.7 g, 145.27 mmol) in acetonitrile (100 mL) in a sealed tube was added Pd(PPh$_3$)$_2$Cl$_2$ (4.2 g, 5.98 mmol) and cuprous iodide (1.14 g, 5.97 mmol). The sealed tube was degassed again and heated at 60° C. for 2 hours. The reaction mixture was cooled and filtered through celite bed. The filtrate was concentrated in vacuum and the residue purified through silica gel (60-120 mesh) column chromatography using petroleum ether to afford methyl 3-fluoro-5-(2-trimethylsilylethynyl)benzoate (14.4 g, 96%) as yellow liquid.

Step 2: To a solution of methyl 3-fluoro-5-(2-trimethylsilylethynyl)benzoate (14.4 g, 57.53 mmol) in methanol (50 mL) was added potassium carbonate (0.7 g 5.14 mmol) and stirred at room temperature for 20 minutes. The reaction mixture was concentrated under reduced pressure. The residue was diluted with ethyl acetate (100 mL), washed with water, brine, dried over anhydrous sodium sulphate and concentrated to yield methyl 3-ethynyl-5-fluoro-benzoate intermediate 4-1 (8.9 g, 87%) as a brown liquid.

Step 3: To a solution of methyl 3-ethynyl-5-fluoro-benzoate (8.9 g, 50 mmol) in tetrahydrofuran (30 mL) and water (15 mL) was added lithium hydroxide (3.1 g, 73.8 mmol) and stirred at room temperature for 3 hours. The reaction mixture was concentrated and acidified with aqueous citric acid solution. The precipitated solid was filtered, washed with water and dried to afford 3-ethynyl-5-fluoro-benzoic acid (7.66 g, 92%) as off white solid.

Step 4: To a solution 3-ethynyl-5-fluoro-benzoic acid (7.6 g, 46.34 mmol), dicyclohexylcarbodiimide (14.4 g, 69.9 mmol) and pentafluorophenol (12.9 g, 70.49 mmol) in tetrahydrofuran (50 mL) was stirred at room temperature for 3 hours. After the completion of the reaction, the mixture was cooled using ice bath and the precipitated dicyclohexylurea was removed by filtration. The filtrate was concentrated and was taken for next step without purification.

Step 5: To a solution of PFP ester (13.9 g, 42.31 mmol) in tetrahydrofuran was added monoboc guanidine (16.3 g, 102.51 mmol) and stirred at room temperature for 4 hours. After completion of reaction, the reaction mixture was evaporated and was purified through silica gel (60-120 mesh) column chromatography using ethyl acetate in petroleum ether to afford tert-butyl N—[N-(3-ethynyl-5-fluorobenzoyl)carbamimidoyl]carbamate intermediate 4 (9.5 g, 75%) as an off white solid.

INTERMEDIATE 5

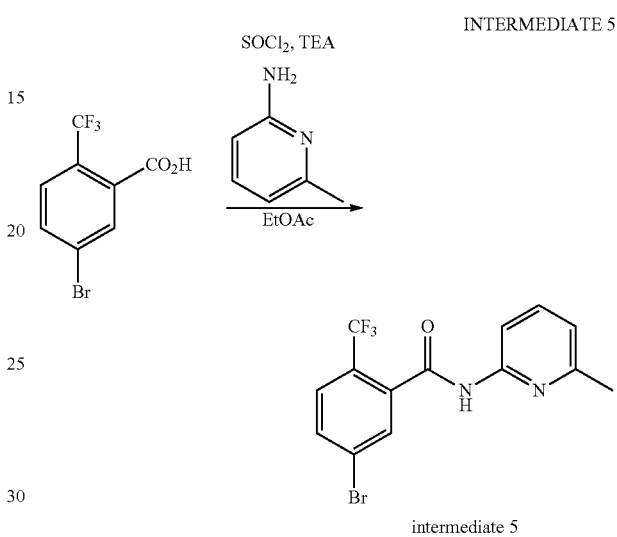

intermediate 5

A solution of 5-bromo-2-(trifluoromethyl) benzoic acid (1.5 g, 7.01 mmol) in thionyl chloride (10 mL) was heated to reflux for 3 hours. The completion of reaction was observed by TLC. The thionyl chloride was evaporated and the residue was charged to the reaction mixture contained 6-methylpyridin-2-amine (0.75 g, 6.93 mmol), triethyl amine (1.7 g, 16.83 mmol) in dry ethyl acetate (25 mL) at 0° C. The reaction mixture was stirred at RT (room temperature) for 12 hours. The completion of reaction was observed by TLC. The reaction mixture was taken in water (200 mL), extracted with ethyl acetate (2×100 mL). The combined organic layer was washed with water (2×100 mL), brine, dried over sodium sulphate and evaporated. The crude was purified by column chromatography using ethyl acetate in petroleum ether to afford 5-bromo-N-(6-methylpyridin-2-yl)-2-(trifluoromethyl)benzamide intermediate 5 (1.1 g, 44%) as yellow solid.

Example 4

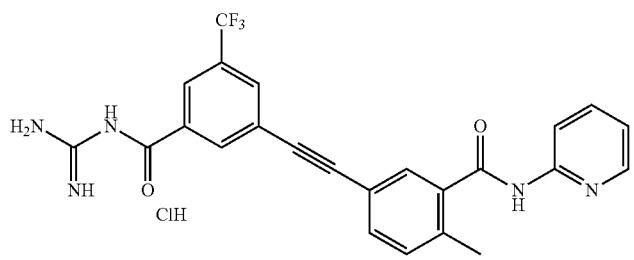

-continued

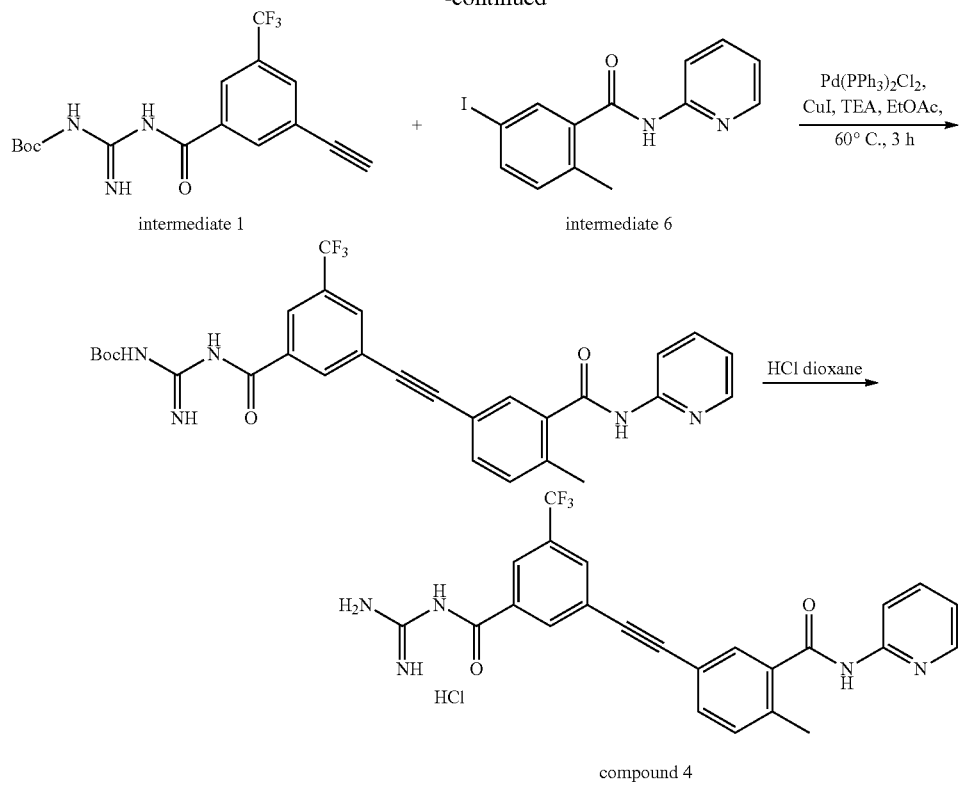

intermediate 1 intermediate 6 compound 4

Step 1: To a degassed solution of tert-butyl N—[N-[3-ethynyl-5-(trifluoromethyl)benzoyl]carbamimidoyl]carbamate intermediate 1 (25 g, 82.84 mmol) and 5-iodo-2-methyl-N-(pyridin-2-yl)benzamide intermediate 6 (32.34 g, 91.12 mmol) in dry ethyl acetate (500 mL) in a sealed tube were added cuprous iodide (0.78 g, 4.14 mmol), triethyl amine (35.92 mL, 248.52 mmol) and bis(triphenylphosphine)palladium(II) dichloride (5.81 g, 8.284 mmol). The reaction mixture was degassed again for 10 min and heated at 65° C. for 5 hours. The completion of reaction was observed by TLC. The reaction mixture was cooled to room temperature and diluted with ethyl acetate and filtered through celite bed. The filtrate was concentrated in vacuum and was purified through silica gel (230-400 mesh) column chromatography using ethyl acetate in petroleum ether to afford 5-[2-[3-(carbamimidoylcarbamoyl)-5-(trifluoromethyl)phenyl]ethynyl]-2-chloro-N-(2-pyridyl)benzamide (20.0 g, 49%) as pale yellow solid.

Step 2: Concentrated HCl (200 mL) was slowly added to –[2-[3-(carbamimidoylcarbamoyl)-5-(trifluoromethyl)phenyl]ethynyl]-2-chloro-N-(2-pyridyl)benzamide (19.0 g, 75.39 mmol) with ice cooling. The resulting suspension was stirred at room temperature for 6 hours. The precipitated solid was filtered, washed successively with water, acetonitrile and ethyl acetate. This material was further dried using lyophilizer for 36 hours to yield 5-((3-(carbamimidoylcarbamoyl)-5-trifluoromethyl)phenyl)ethynyl)-2-methyl-N-(pyridin-2-yl)benzamide hydrochloride compound 4 (15.0 g, 89%) as off white solid.

$^1$H NMR: 400 MHz, DMSO-d6: δ 12.32 (s, 1H), 11.12 (s, 1H), 8.65-0.00 (m, 4H), 8.53 (s, 1H), 8.44 (s, 1H), 8.40 (d, J=4.20 Hz, 1H), 8.31 (s, 1H), 8.16 (d, J=8.36 Hz, 1H), 7.91-7.95 (m, 1H), 7.78 (s, 1H), 7.66 (d, J=7.80 Hz, 1H), 7.43 (d, J=8.16 Hz, 1H), 7.25-7.22 (m, 1H), 2.45 (s, 3H).

LC-MS APCI: Calculated for $C_{24}H_{18}F_3N_5O_2$ 465.44; Observed m/z [M+H]+466.0.

Purity by LC-MS: 99.92%.

Purity by HPLC: 96.58%.

INTERMEDIATE 6

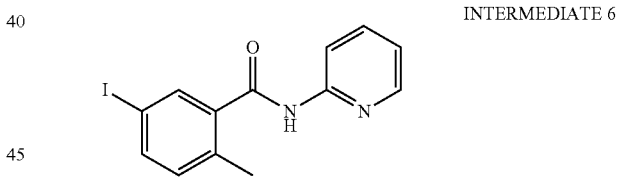

Step 1: To the stirred solution of 2-methyl benzoic acid (50.0 g, 367.6 mmol) in conc. $H_2SO_4$ (500 mL) was added N-iodosuccinimide (78.6 g, 349.2 mmol) slowly at 0° C. The reaction was stirred at 0° C. for 5 hours. After completion of the reaction it was quenched with ice. The solid precipitated was filtered, washed with water and dried under vacuum to yield 5-iodo-2-methylbenzoic acid (70.0 g, 74%) as pale brown solid.

Step 2: A solution of 5-iodo-2-methylbenzoic acid (50.0 g, 190.0 mmol) in thionyl chloride (250 mL) was heated at reflux for 3 hours. The completion of reaction was observed by TLC (by converting acid chloride to methyl ester). The thionyl chloride was evaporated and the residue was charged to the reaction mixture contained 2-amino pyridine (19.72 g, 209.8 mmol), triethyl amine (82.75 mL, 572.5 mmol) in dry ethyl acetate (500 mL) at 0° C. The reaction mixture was stirred at RT (room temperature) for 12 hours. The completion of reaction was observed by TLC. The reaction mixture was taken in water (2000 mL), extracted with ethyl acetate (2×1000 mL). The combined organic layer was washed with water (2×1000 mL), brine, dried over sodium sulphate and evaporated. The crude material was purified by column chromatography using ethyl acetate in petroleum ether to afford 5-iodo-2-methyl-N-(pyridin-2-yl)benzamide intermediate 6 (30.0 g, 48%) as pale yellow solid.

Example 5

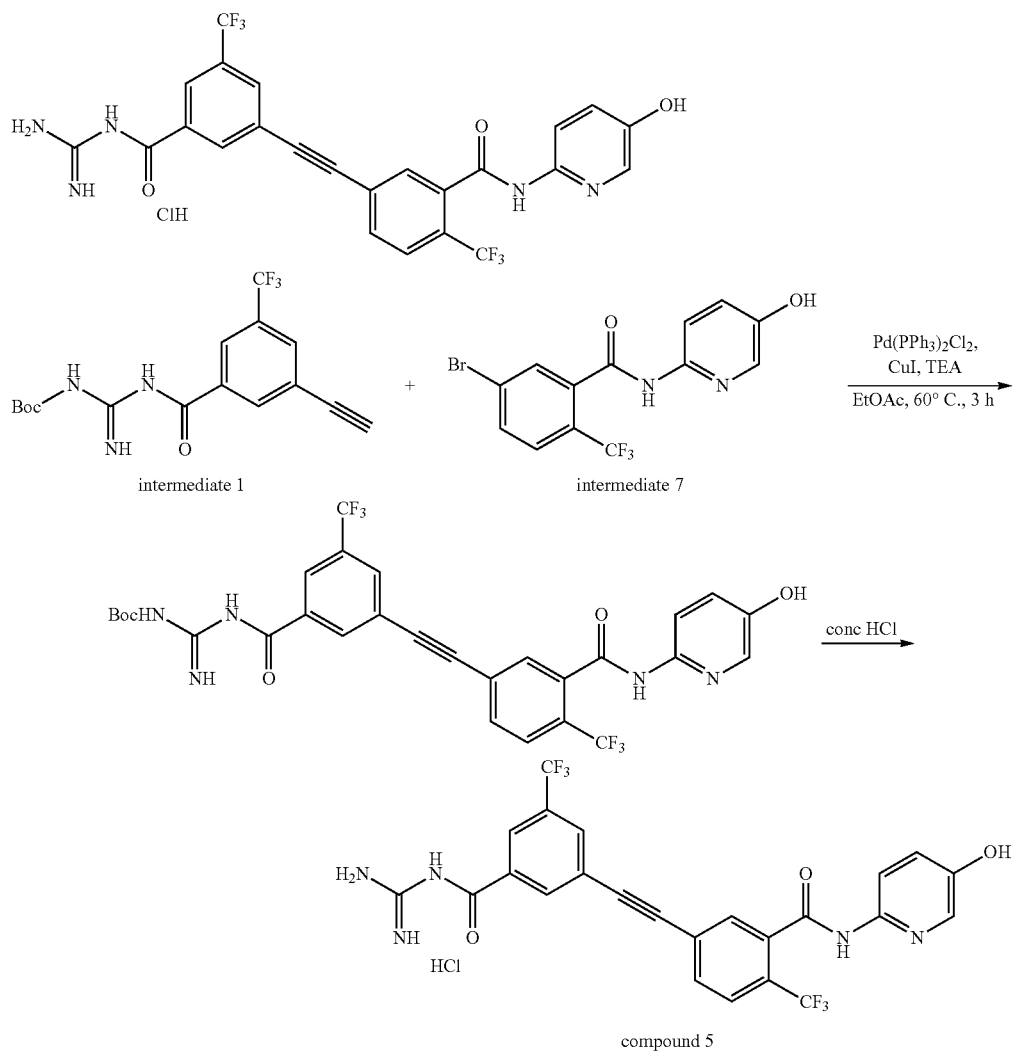

Step 1: To a degassed solution of 5-Bromo-N-(5-hydroxy-pyridin-2-yl)-2-trifluoromethyl-benzamide intermediate 7 (1.0 g, 2.77 mmol) and tert-butyl N—[N-[3-ethynyl-5-(trifluoromethyl)benzoyl]carbamimidoyl]carbamate intermediate 1 (0.93 g, 3.04 mmol) in dry ethyl acetate (15 mL) in a round bottom flask were added cuprous iodide (26 mg, 0.14 mmol), triethyl amine (1.2 mL, 8.31 mmol) and bis(triphenylphosphine)palladium(II) dichloride (194 mg, 0.27 mmol). The reaction mixture was degassed again for 10 min and heated at 65° C. for 5 hours. The completion of reaction was observed by TLC. The reaction mixture was cooled, diluted with ethyl acetate and filtered through celite bed. The filtrate was concentrated under vacuum and the crude material was purified through silica gel (230-400 mesh) column chromatography using 70-80% ethyl acetate in petroleum ether to afford 5-[2-[3-(carbamimidoylcarbamoyl)-5 (trifluoromethyl)phenyl]ethynyl]-N-(5-hydroxy-2-pyridyl)-2-(trifluoromethyl)benzamide (600.0 mg, 36%) as an off white solid.

Step 2: The solid compound 5-[2-[3-(carbamimidoylcarbamoyl)-5-(trifluoromethyl)phenyl]ethynyl]-N-(5-hydroxy-2-pyridyl)-2-(trifluoromethyl)benzamide hydrochloride (600.0 mg, 0.79 mmol) was taken in concentrated HCl (5 mL) and stirred overnight at room temperature. The solids formed were filtered, washed with water, hexane and dried under vacuum to afford 5-((3-(carbamimidoylcarbamoyl)-5-(trifluoromethyl)phenyl)ethynyl)-N-(5-hydroxypyridin-2-yl)-2-(trifluoromethyl)benzamide hydrochloride compound 5 (450 mg, 83%) as an off white solid.

$^1$H NMR 400 MHz, DMSO-d6: δ 12.44 (s, 1H), 11.09 (s, 1H), 8.68 (s, 5H), 8.51 (s, 1H), 8.37 (s, 1H), 7.89-7.96 (m, 5H), 7.34 (dd, J=2.40, 8.80 Hz, 1H).

LC-MS APCI: Calculated for $C_{24}H_{15}F_6N_5O_3$ 535.41; Observed m/z $[M+H]^+$ 536.

Purity by LC-MS: 95.65%.

Purity by HPLC: 93.96%.

INTERMEDIATE 7

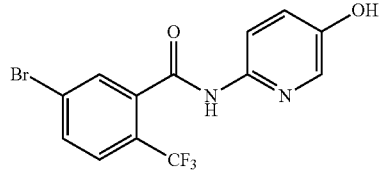

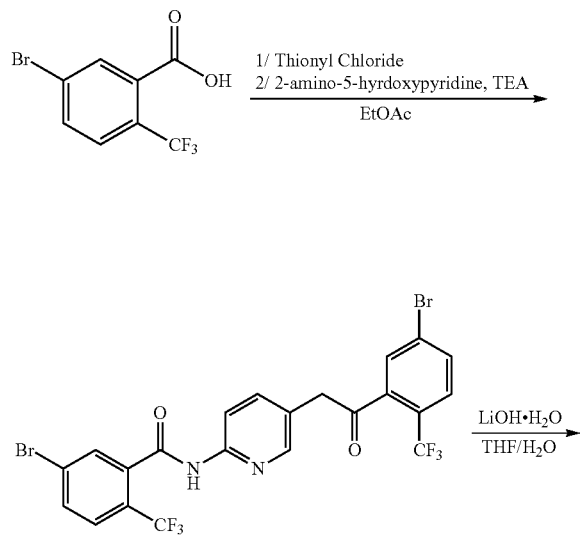

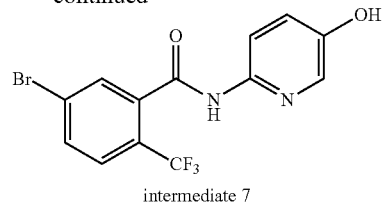

intermediate 7

Step 1: To a solution of 5-Bromo-2-trifluoromethyl-benzoic acid (10.0 g, 37.17 mmol) in dry dichloromethane was added thionyl chloride (22.11 g, 185.85 mmol) at 0° C. The mixture was then heated at 80° C. for 3 hours. After completion of the reaction it was concentrated under reduced pressure. To the cooled solution of acid chloride in ethyl acetate under nitrogen atmosphere was added triethylamine (16.11 ml, 111.51 mmol) and 2-amino 5-hydroxy pyridine (2.04 g, 18.58 mmol). The reaction mixture was stirred at room temperature for 12 hours. The reaction mixture was concentrated, diluted with ethyl acetate, washed with water, dried over $Na_2SO_4$ and concentrated under vacuum. The residue was purified through silica gel (60-120 mesh) column chromatography using 8-12% ethyl acetate in petroleum ether to afford 5-Bromo-2-trifluoromethyl-benzoic acid 6-(5-bromo-2-trifluoromethyl-benzoylamino)-pyridin-3-yl ester (6.0 g, 26%).

Step 2: To an ice cooled solution of 5-Bromo-2-trifluoromethyl-benzoic acid 6-(5-bromo-2-trifluoromethyl-benzoylamino)-pyridin-3-yl ester (6.0 g, 9.85 mmol) in tetrahydrofuran (25 mL) and water (12.5 mL), was added lithium hydroxide (0.5 g, 11.82 mmol) and stirred at room temperature for 3 hours. The reaction mixture was concentrated and extracted with ethyl acetate. Organic layer was separated, washed with water, dried over $Na_2SO_4$ and concentrated under vacuum. The residue was purified through silica gel (60-120 mesh) column chromatography using 70-80% ethyl acetate in petroleum ether to afford 5-Bromo-N-(5-hydroxypyridin-2-yl)-2-trifluoromethyl-benzamide intermediate 7 (3.0 g, 88%) as white solid.

Example 6

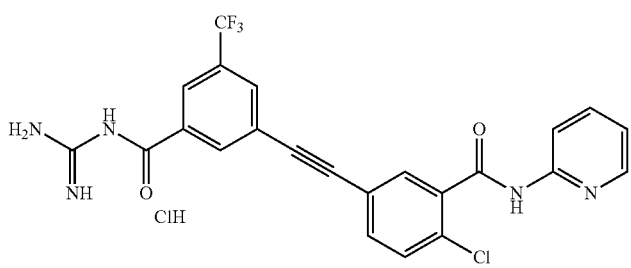

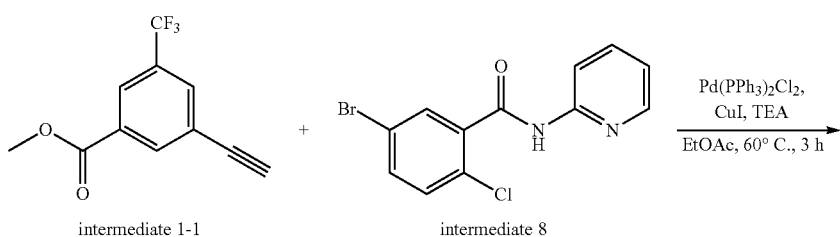

intermediate 1-1     intermediate 8

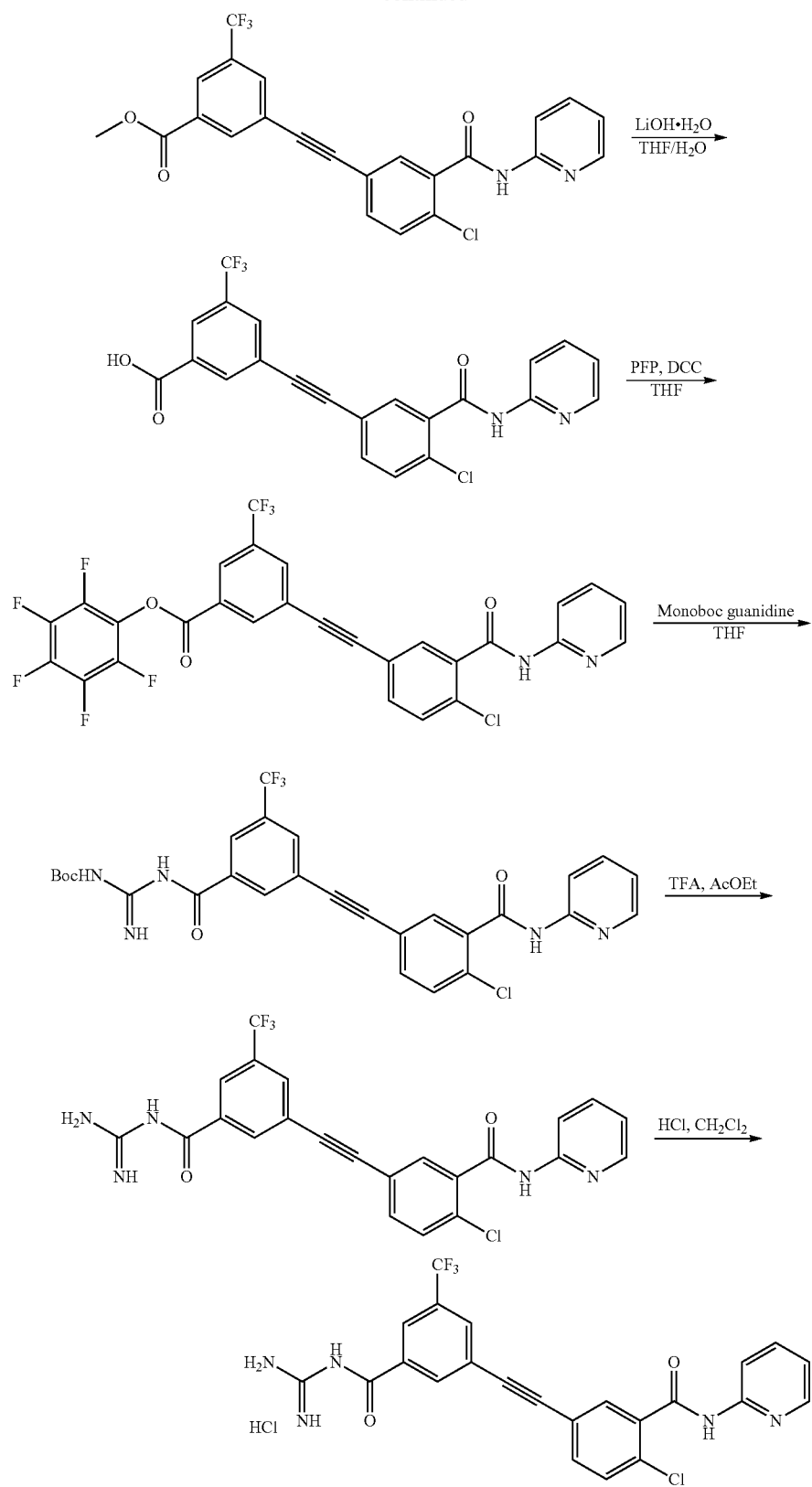

Step 1: To a degassed solution of methyl 3-ethynyl-5-(trifluoromethyl)benzoate intermediate 1-1 (0.8 g, 3.53 mmol), 5-bromo-2-chloro-N-(pyridin-2-yl)benzamide intermediate 8 (1.1 g, 3.53 mmol) and triethylamine (1.5 mL, 10.6 mmol) in ethyl acetate (20 mL) in a sealed tube was added Pd(PPh$_3$)$_2$Cl$_2$ (0.25 g, 0.35 mmol) and cuprous iodide (0.033 g, 0.18 mmol). The reaction mixture was degassed again and heated at 60° C. for 5 hours. The reaction mixture was cooled, diluted with ethyl acetate and filtered through celite. The filtrate was concentrated in vacuo. The residue was purified through silica gel (60-120 mesh) column chromatography using 20-35% ethyl acetate in petroleum ether to afford methyl 3-[2-[4-chloro-3-(2-pyridylcarbamoyl)phenyl]ethynyl]-5-(trifluoromethyl)benzoate (0.55 g, 31%).

Step 2: To an ice cooled solution of methyl 3-[2-[4-chloro-3-(2-pyridylcarbamoyl)phenyl]ethynyl]-5-(trifluoromethyl)benzoate (0.55 g, 1.2 mmol) in tetrahydrofuran (8 mL) and water (4 mL), was added lithium hydroxide monohydrate (0.15 g, 3.6 mmol) and stirred at room temperature for 4 hours. The reaction mixture was concentrated and acidified with aqueous citric acid solution. The solid precipitated out was filtered, washed with water and dried to afford 3-[2-[4-chloro-3-(2-pyridylcarbamoyl)phenyl]ethynyl]-5-(trifluoromethyl)benzoic acid (0.4 g, 75%) as off white solid.

Step 3: A mixture of 3-[2-[4-chloro-3-(2-pyridylcarbamoyl)phenyl]ethynyl]-5-(trifluoromethyl)benzoic acid (0.4 g, 0.79 mmol), dicyclohexylcarbodiimide (0.24 g, 1.18 mmol) and pentafluorophenol (0.21 g, 1.18 mmol) in anhydrous tetrahydrofuran (5 mL) was stirred at room temperature for 3 hours. After completion of reaction, the mixture was cooled using ice bath and the precipitated dicyclohexylurea was removed by filtration. The filtrate was concentrated. The residue was purified through silica gel (60-120 mesh) column chromatography using 20-35% ethyl acetate in petroleum ether to afford (2,3,4,5,6-pentafluorophenyl) 3-[2-[4-chloro-3-(2-pyridylcarbamoyl)phenyl]ethynyl]-5-(trifluoromethyl)benzoate (0.4 g, 72%).

Step 4: To a solution of (2,3,4,5,6-pentafluorophenyl) 3-[2-[4-chloro-3-(2-pyridylcarbamoyl)phenyl]ethynyl]-5-(trifluoromethyl)benzoate (0.4 g, 0.65 mmol) in anhydrous tetrahydrofuran (5 mL) was added monoboc guanidine (0.16 g, 0.98 mmol) and stirred at room temperature for 8 hours. After completion of reaction, the reaction mixture was evaporated and purified through silica gel (230-400 mesh) column chromatography using 30-40% ethyl acetate in petroleum ether to afford tert-butyl N—[N-[3-[2-[4-chloro-3-(2-pyridylcarbamoyl)phenyl]ethynyl]-5-(trifluoromethyl)benzoyl]carbamimidoyl]carbamate (0.2 g, 52%) as white solid.

Step 5: Trifluoro acetic acid (0.8 g, 6.83 mmol) was added to a cooled solution of tert-butyl N—[N-[3-[2-[4-chloro-3-(2-pyridylcarbamoyl)phenyl]ethynyl]-5-(trifluoromethyl)benzoyl]carbamimidoyl]carbamate (0.2 g, 0.34 mmol) in dichloromethane (5 mL) and stirred at room temperature for 6 hours. After completion of reaction, the reaction mixture was evaporated. The residue was stirred in 10% NaHCO$_3$ solution till the pH of medium changed basic. Filtered off the solid and washed with water and hexane, dried under vacuum. The solid was taken in diethyl ether (5 mL), added HCl in diethyl ether (3 mL) and stirred at room temperature for 3 hours. The reaction mixture was evaporated under vacuum. The solid formed was triturated with diethyl ether and filtered to yield 5-((3-(carbamimidoylcarbamoyl)-5-(trifluoromethyl)phenyl)ethynyl)-2-chloro-N-(pyridin-2-yl)benzamide hydrochloride compound 6 (0.11 g, 67%) as off white solid (Hydrochloride salt).

1H NMR (400 MHz, DMSO-d6): δ 12.30 (d, J=2.80 Hz, 1H), 11.20 (s, 1H), 8.63 (s, 4H), 8.54 (s, 1H), 8.45 (s, 1H), 8.38 (d, J=3.60 Hz, 1H), 8.33 (s, 1H), 8.17 (d, J=6.80 Hz, 1H), 7.87-7.91 (m, 2H), 7.71-7.74 (m, 1H), 7.56-7.67 (m, 1H), 7.21 (t, J=7.20 Hz, 1H).

LC-MS APCI: Calculated for C$_{23}$H$_{15}$ClF$_3$N$_5$O$_2$ 485.85; Observed m/z [M+H]+486.

Purity by LC-MS: 95.22%.

Purity by HPLC: 97.05%. RT: 12.60.

INTERMEDIATE 8

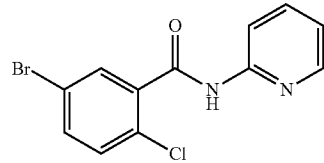

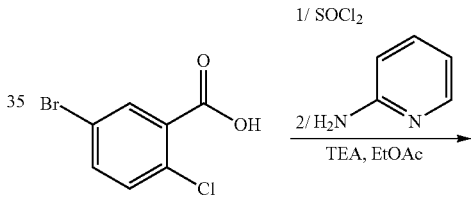

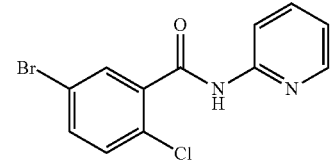

A solution of 5-bromo-2-chlorobenzoic acid (5.0 g, 21.23 mmol) in thionyl chloride (15 mL) was heated at reflux for 3 hours. The completion of reaction was observed by TLC. The thionyl chloride was evaporated and the residue was charged to the reaction mixture containing 2-amino pyridine (2.20 g, 23.35 mmol), triethyl amine (9.2 mL, 63.69 mmol) in dry ethyl acetate (30 mL) at 0° C. The reaction mixture was stirred at room temperature for 12 hours. The completion of reaction was observed by TLC. The reaction mixture was taken in water (100 mL), extracted with ethyl acetate (2×100 mL). The combined organic layer was washed with water (2×100 mL), brine, dried over sodium sulphate and evaporated. The crude material was purified by column chromatography using ethyl acetate in petroleum ether to afford the 5-bromo-2-chloro-N-(pyridin-2-yl)benzamide intermediate 8 (3.0 g, 46%) as brown solid.

Example 7
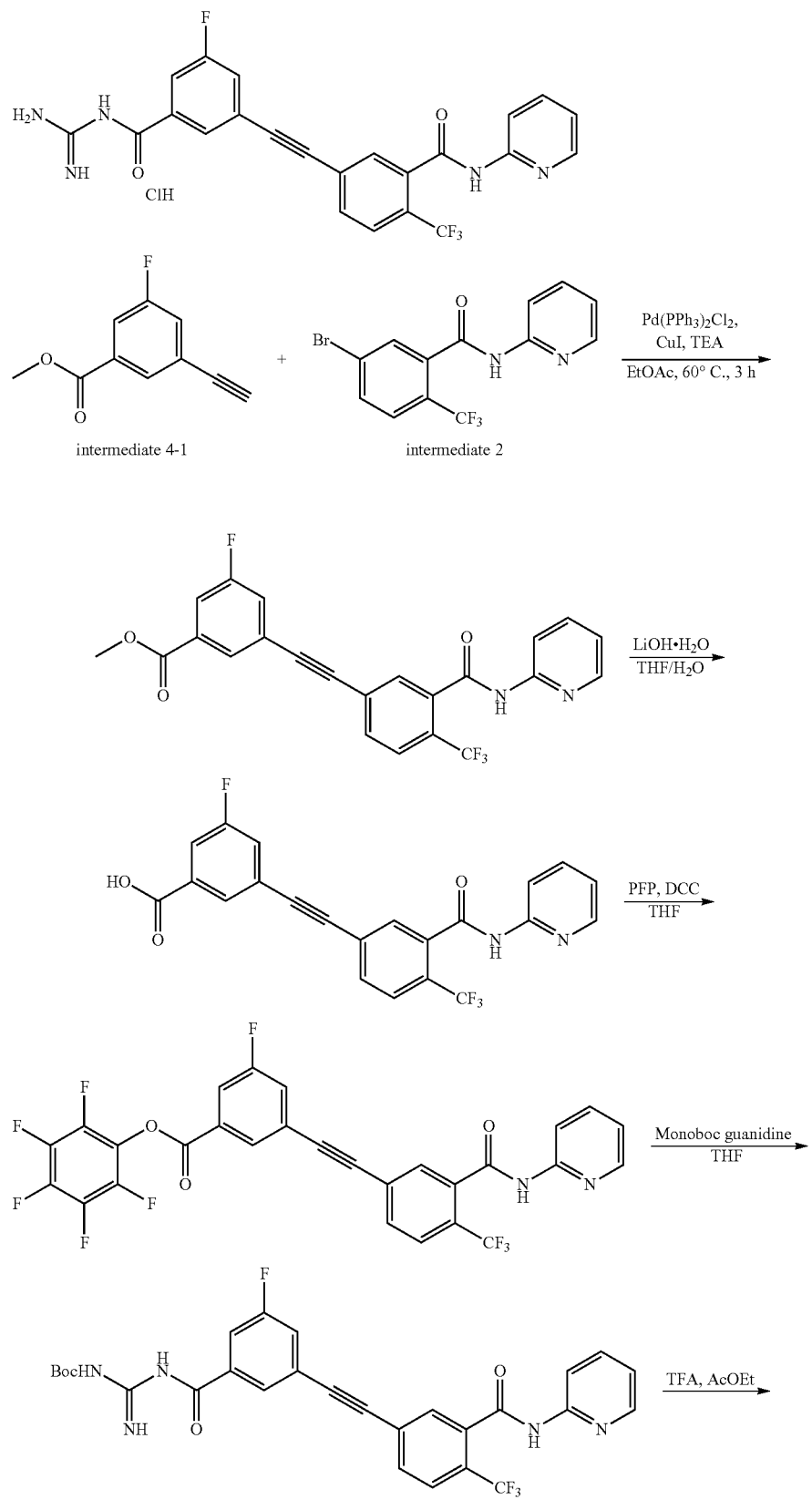

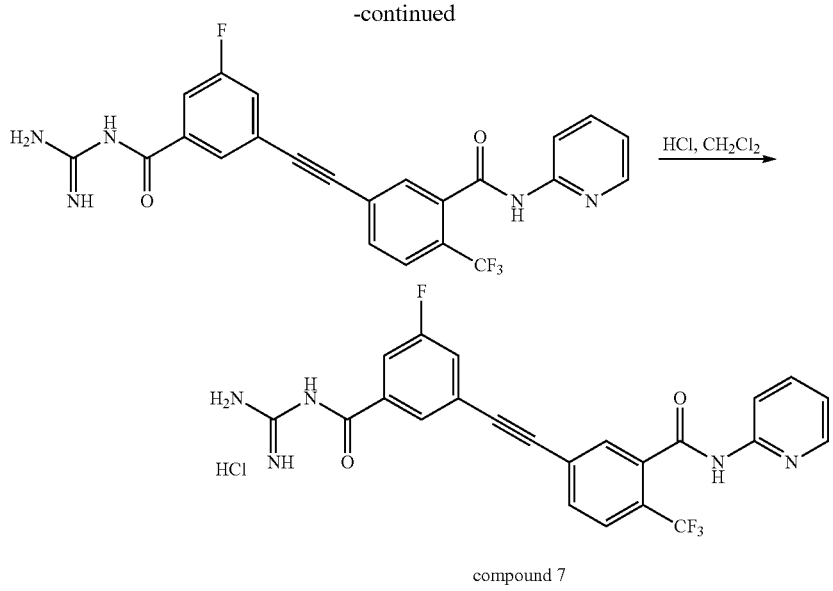

compound 7

Step 1: To a degassed solution of methyl 3-ethynyl-5-fluorobenzoate intermediate 4-1 (0.4 g, 1.159 mmol) and 4-bromo-N-(pyridin-2-yl)-2-(trifluoromethyl)benzamide intermediate 2 (0.2 g, 1.122 mmol) in dry ethyl acetate (15 mL) in a sealed tube were added cuprous iodide (0.01 g, 0.057 mmol), triethyl amine (0.29 mL, 2.87 mmol) and bis(triphenylphosphine)palladium(II) dichloride (0.084 g, 0.116 mmol). The reaction mixture was degassed again for 10 min and heated at 60° C. for 2 hours. The completion of reaction was observed by TLC. The reaction mixture was cooled to room temperature, diluted with ethyl acetate and filtered through celite bed. The filtrate was concentrated in vacuo and was purified through silica gel (230-400 mesh) column chromatography using ethyl acetate in petroleum ether to afford 3-Fluoro-5-[3-(pyridin-2-ylcarbamoyl)-4-trifluoromethyl-phenylethynyl]-benzoic acid methyl ester (0.4 g, 74%) as off white solid.

Step 2: To an ice cooled solution of 3-Fluoro-5-[3-(pyridin-2-ylcarbamoyl)-4-trifluoromethyl-phenylethynyl]-benzoic acid methyl ester (0.4 g, 0.904 mmol) in tetrahydrofuran (10 mL) and water (5 mL), was added lithium hydroxide (0.11 g, 2.738 mmol) and stirred at room temperature for 3 hours. The reaction mixture was concentrated and acidified with aqueous citric acid solution and extracted with ethyl acetate (50 mL). The combined organic layer was washed with water, brine, dried over anhydrous sodium sulphate and concentrated to yield 3-Fluoro-5-[3-(pyridin-2-ylcarbamoyl)-4-trifluoromethyl-phenylethynyl]-benzoic acid (0.19 g, 50%) as pale brown solid.

Step 3: A solution of 3-Fluoro-5-[3-(pyridin-2-ylcarbamoyl)-4-trifluoromethyl-phenylethynyl]-benzoic acid (0.19 g, 0.445 mmol), dicyclohexylcarbodiimide (0.14 g, 0.68 mmol) and pentafluorophenol (0.12 g, 0.68 mmol) in tetrahydrofuran (10 mL) was stirred at room temperature for 2 hours. After the completion of the reaction, the mixture was cooled using ice bath and the precipitated dicyclohexylurea was removed by filtration. The obtained filtrate was concentrated and was taken for next step without further purification to give (2,3,4,5,6-pentafluorophenyl) 3-fluoro-5-[2-[3-(2-pyridylcarbamoyl)-4-(trifluoromethyl)phenyl]ethynyl]benzoate.

Step 4: To a solution of (2,3,4,5,6-pentafluorophenyl) 3-fluoro-5-[2-[3-(2-pyridylcarbamoyl)-4-(trifluoromethyl)phenyl]ethynyl]benzoate (0.13 g, 0.218 mmol) in tetrahydrofuran was added monoboc guanidine (0.053 g, 0.33 mmol) and stirred at room temperature for 6 hours. After completion of reaction, the reaction mixture was evaporated and the residue was purified through silica gel (60-120 mesh) column chromatography using ethyl acetate in petroleum ether to afford tert-butyl N—[N-[3-[2-[3-(2-pyridylcarbamoyl)-4-(trifluoromethyl)phenyl]ethynyl]-5-fluorobenzoyl]carbamimidoyl]carbamate (0.05 g, 41%) as off white solid.

Step 5: To an ice cooled solution of tert-butyl N—[N-[3-[2-[3-(2-pyridylcarbamoyl)-4-(trifluoromethyl)phenyl]ethynyl]-5-fluorobenzoyl]carbamimidoyl]carbamate (0.05 g, 0.23 mmol) in dry dichloromethane (10 mL) was added trifluoroacetic acid (0.25 g, 2.196 mmol) and stirred at room temperature for 6 hours. The completion of reaction was observed by TLC. The reaction mixture was evaporated and triturated with diethyl ether, obtained solid was filtered and washed with diethyl ether to afford the salt as off white solid. This was taken in 10% $NaHCO_3$ solution and stirred at room temperature until the pH changed to basic. The solid was filtered, washed with water and dried under vacuum. The solid was taken in diethyl ether (10 mL), added HCl in diethyl ether (5 mL) and stirred for 1 hour. The solid was filtered, washed with hexane and dried under vacuum to afford 5-((3-(carbamimidoylcarbamoyl)-5-fluorophenyl)ethynyl)-N-(pyridin-2-yl)-2-(trifluoromethyl)benzamide hydrochloride compound 7 (0.04 g, 75%) as an off white solid.

$^1$H NMR (400 MHz, DMSO-d6): δ 11.99 (s, 1H), 11.22 (s, 1H), 8.52 (m, 4H), 8.38 (s, 1H), 8.14-8.17 (m, 2H), 7.99-7.86 (m, 5H), 7.21 (t, J=6.00 Hz, 1H).

LC-MS APCI: Calculated for $C_{23}H_{15}F_4N_5O_2$ 469.40; Observed m/z [M+H]$^+$470.0.

Purity by LC-MS: 98.90%.

Purity by HPLC: 97.9%.

Example 8

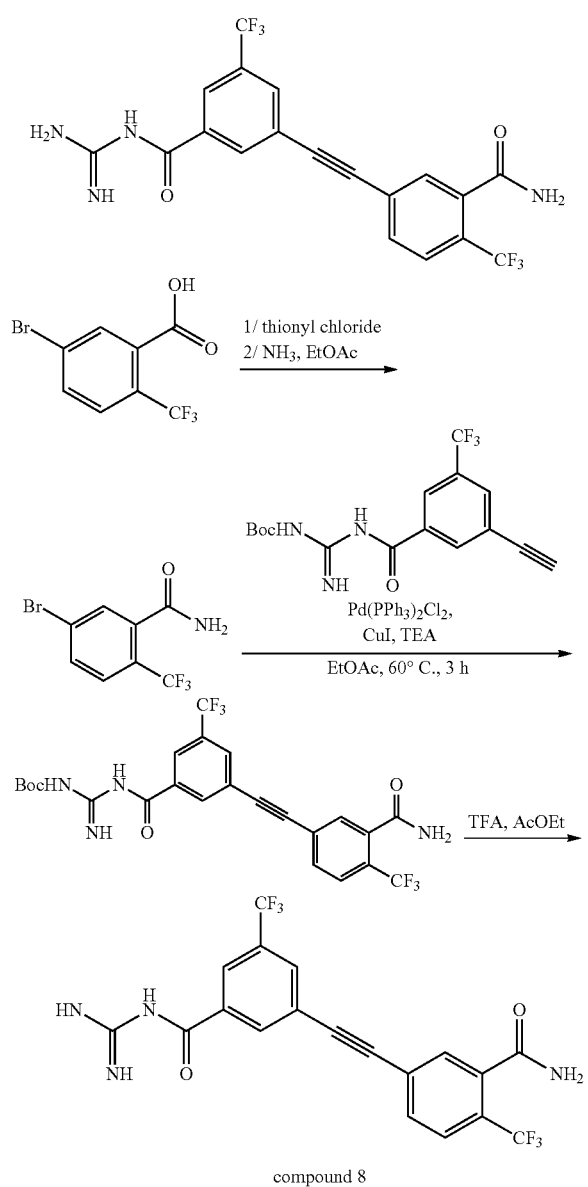

compound 8

Step 1: A solution of 5-bromo-2-(trifluoromethyl)benzoic acid (2.0 g, 7.43 mmol) in thionyl chloride (4.42 g, 37.17 mmol) was heated at reflux for 3 hours. The completion of reaction was observed by TLC (by converting acid chloride to methyl ester). Thionyl chloride was evaporated and the residue was taken in ethyl acetate, purged with ammonia gas for 15 min at 0° C. Then the reaction was stirred at room temperature for 1 hour. The completion of reaction was observed by TLC. The reaction mixture was taken in water (50 mL) and extracted with ethyl acetate (2×100 mL). The combined organic layer was washed with water (2×50 mL), brine, dried over sodium sulfate and evaporated to get crude product. The crude material was purified by silica gel (60-120 mesh) column chromatography using ethyl acetate in petroleum ether to afford 5-bromo-2-(trifluoromethyl) benzamide (1.5 g, 75%) as white solid.

Step 2: To a degassed solution of 5-bromo-2-(trifluoromethyl)benzamide (0.5 g, 1.86 mmol) and tert-butyl N—[N-[3-ethynyl-5-(trifluoromethyl)benzoyl]carbamimidoyl]carbamate intermediate 1 (0.65 g, 1.86 mmol) in dry ethyl acetate (10 mL) were added cuprous iodide (0.018 g, 0.09 mmol), triethyl amine (0.78 mL, 5.59 mmol) and bis(triphenylphosphine)palladium(II) dichloride (0.06 g, 0.09 mmol). The reaction mixture was degassed again for 10 min and heated at 65° C. for 5 hours. The completion of reaction was observed by TLC. The reaction mixture was cooled to room temperature, diluted with ethyl acetate and filtered through celite bed. The filtrate was concentrated in vacuum and was purified through silica gel (230-400 mesh) column chromatography using ethyl acetate in petroleum ether to afford tert-butyl N—[N-[3-[2-[3-carbamoyl-4-(trifluoromethyl)phenyl]ethynyl]-5 (trifluoromethyl)benzoyl]carbamimidoyl]carbamate (0.3 g, 30%) as off white solid.

Step 3: To an ice cooled solution of tert-butyl N—[N-[3-[2-[3-carbamoyl-4-(trifluoromethyl)phenyl]ethynyl]-5-(trifluoromethyl)benzoyl]carbamimidoyl]carbamate (0.3 g, 0.55 mmol) in dry dichloromethane (5 mL) was added trifluoroacetic acid (1.26 g, 11.07 mmol) and stirred at room temperature for 16 hours. The completion of reaction was observed by TLC. The reaction mixture was evaporated and basified with ice cooled 10% $NaHCO_3$ solution. The compound was extracted with ethyl acetate. The combined organic layer was washed with water, brine, dried over sodium sulfate and evaporated to get crude product. Purification of the material by silica gel (230-400 mesh) column chromatography using ethyl acetate in petroleum ether, yielded the pure N-carbamimidoyl-3-(3-carbamoyl-4-(trifluoromethyl)phenyl)ethynyl)-5-trifluoromethyl)benzamide compound 8 (0.09 g, 37%) as white solid.

NMR: 400 MHz, DMSO-d6: δ 8.51 (s, 1H), 8.40 (s, 1H), 8.10 (s, 1H), 8.07 (s, 1H), 7.86 (s, 2H), 7.80 (s, 1H), 7.72 (s, 1H), 6.88 (s, 1H).

LC-MS APCI: Calculated for $C_{19}H_{12}F_6N_4O_2$ 442.32; Observed m/z [M+H]+443.0.

Purity by LC-MS: 95.93%.

Purity by HPLC: 98.41%.

Assays of Biological Activity of Compounds of the Invention

1) In Vitro Activities of Compounds No 1 (Including Compounds 1a, 1b and 1c) to 8 (*P. Falciparum*)

The biological activity of compounds of formula (I) according to the invention has been tested on the basis of an $IC_{50}$ evaluation against the strain NF54 of *P. falciparum*.

a) Parasitic Culture:

For Hypoxanthine assay, parasite cultures were grown in 100 mm petri-dishes in growth media having 5% haematocrit in tri-gas incubator (Cat #3131, Thermo Scientific Forma Series II Water Jacketed $CO_2$ incubator, sold by Thermofisher) having controlled gas mixtures of 4% $CO_2$ and 3% $O_2$ at temperature 37° C.

Parasite growth and morphology was observed daily using thin smears at 100× (oil immersion) magnification following staining with Giemsa stain.

Parasites use hypoxanthine included in the growth media as a precursor in nucleic acid synthesis. Accordingly, by replacing hypoxanthine in the media by a radioactive hypoxanthine, such as $^3$H-hypoxanthine as indicated here-under, the rate of DNA replication and growth rate of the parasites can be measured, in particular in the presence of the tested compounds of the invention.

b) Materials & Methods:
(i) Growth Media

The growth media used for the above-indicated parasites contains 1 L of RPMI-1640 (sold by Invitrogen), 5 mg of Albumax II (sold by Invitrogen), 5 mg of Hypoxanthine (sold by Sigma), 25 mM Hepes (sold by Invitrogen) and 2.5 mg of Gentamycin (sold by Sigma).

(ii) Screening Media

The screening media used contains 1 L of RPMI-1640 (sold by Invitrogen), 5 mg of Albumax II (sold by Invitrogen), 25 mM Hepes (sold by Invitrogen) and 2.5 mg of Gentamycin (sold by Sigma).

(iii) Assay Reagents

For this assay, the above described screening media was used, as well as 20 Ci/mmol of a radioactive hypoxanthine (the ligand $^3$H-hypoxanthine (20 Ci/mmol, 1 mCi/mL) sold by the American Radiolabeled Chemicals (ARC) from St Louis, Mo.), some Top Seal A (sold by Perkin Elmer), 96 Well Cell Culture plates (CellStar® sold by Greiner Bio-One GmbH), MicroScint® 20 (sold by Perkin Elmer) and GFB plates (sold by Perkin Elmer).

On each 96 well plate, 3 compounds of formula (I) according to the invention as well as one standard compound (positive control) are each tested in 12 wells in duplicate.

Said standard compound is a mixture of Artesunate and Chloroquine, two well-known anti malaria compounds.

The maximum activity value of the parasites is determined as positive control by observing the parasites in the presence of erythrocytes, while the minimum activity value of the parasites is determined in a negative control by observing the erythrocytes in the absence of parasites.

The tested compounds of the invention were assayed at a final concentration of 10 μM.

In order to do so, stock solutions at a concentration of 40 μM of compound to be tested are made available in high recovery vials at a concentration of 10 mM. From this, a 20 μM stock in Screening media is prepared (0.4 μl of 10 mM compound+996 μl of screening media) to keep % DMSO at 0.4.

Starting from 20 μM stock solution, 100 μl is added in the assay plate already containing 100 μl of screening media and 1:2 fold serial 12 point dilutions are made in the plate (10 μM to 4.8 nM) (100 μl of compound is mixed with 100 μl of screening media already present in plates, and so on).

c) Assay Procedure

*P. falciparum* culture diluted to 0.3% p and 1.25% h—synchronous ring stage. The assay was carried out in sterile, in the 96-well plate.

Compounds were diluted to the final required concentration so that the DMSO concentration in the well does not exceed 0.1%.

100 μL of *P. falciparum* culture was added per well and were then incubated at 37° C. for 48 hours. Smears are then made to check for growth of culture control after 48 hours of incubation.

Once ensured that the culture has grown in % p, 50 μL of 3H-Hypoxanthine (0.5 μCi/well) is added in each well, and the assay plate is further incubated for 24 hours.

After 72 hours, the assay plates are harvested on GFB plates. In order to remove nonspecific binding, the plates are washed with 2.5 ml of cooled distilled water and GFB plates were kept for drying at 37° C. over night or 60° C. for 1 hour.

50 μL of Microscint®-20 was added to each well.

The plates are then read in Top Count (45 sec/well).

The assay data were analysed using Graph pad prism ver.5 software. A variable sigmoid dose response curve is plotted keeping log concentrations at X-axis and % inhibition at Y-axis.

d) Results

TABLE 2

| Compound No | NF54 IC50 (nM) |
|---|---|
| 1a | <10 |
| | Measured values are equal to 7 nM |
| 1b | <15 |
| | Measured values are between 3 and 12 nM |
| 1c | <20 |
| | Measured values are equal to 17 nM |
| 2 | <25 |
| 3 | <25 |
| 4 | <10 |
| 5 | <10 |
| 6 | <10 |
| 7 | <20 |
| 8 | <100 |

The IC50 value indicates the concentration of compound that causes a fifty percent growth inhibition of the parasite compared to the positive control.

All the tested compounds of formula (I) according to the invention are indeed able to inhibit the activity of the parasites and show an inhibitory activity against *P. falciparum*.

Good results are in particular obtained with compounds no 1-7, particularly with compounds no 1 (1a, 1b, 1c), 4, 5 and 6. The most preferred compounds are 1 (1a, 1b, 1c) and 4.

2) In Vitro Activity on Field Clinical Isolates (*P. Vivax* and *P. Falciparum*)

The biological activity of compound 1b according to the invention has been tested on the basis of an IC50 evaluation against the strain *P. vivax*.

a) Parasitic Culture: Field Location and Sample Collection

*Plasmodium* isolates were collected from patients attending malaria clinics in Timika (Papua, Indonesia), a region endemic for multidrug-resistant strains of *P. vivax* and *P. falciparum*. Patients with symptomatic malaria presenting to an outpatient facility were recruited into the study if singly infected with *P. falciparum* or *P. vivax*, with a parasitaemia of between 2,000 μl and 80,000 μl, and the majority (>60%) of parasites at ring stage of development. Venous blood (5 mL) was collected by venepuncture and after removal of host white blood cells by using Plasmodipur filters (Euro-Proxima B.V., The Netherlands), packed infected red blood cells (iRBCs) were used for the ex vivo drug susceptibility assay.

b) Ex Vivo Drug Susceptibility Assay
(i) Materials & Methods:

Standard anti-malarial drugs chloroquine (CQ), piperaquine (PIP), mefloquine (MFQ), and artesunate (AS) (WWARN QA/QC Reference Material Program), and experimental compound 1b were prepared as 1 mg/mL stock solutions in H$_2$O or dimethyl sulfoxide (DMSO) according to the manufacturers' instructions. Drug plates were pre-dosed by diluting the compounds in 50% Methanol followed by lyophilisation and stored at 4° C.

(ii) Assay Procedure

Drug susceptibility of *P. vivax* and *P. falciparum* isolates was measured using a protocol modified from the WHO microtest (see for instance in Marfurt J. et al., Antimicrob Agents Chemother. 2011 September; 55(9):4461).

Two hundred μL of a 2% haematocrit Blood Media Mixture (BMM), consisting of RPMI 1640 medium plus 10% $AB_+$ human serum (*P. falciparum*) or McCoy's 5A medium plus 20% $AB_+$ human serum (*P. vivax*) was added to each well of pre-dosed drug plates containing 11 serial concentrations (2-fold dilutions) of the anti-malarials (maximum concentration shown in brackets) CQ (2,993 nM), PIP (1,029 nM), MFQ (338 nM), AS (49 nM), and compound 1b (237 nM). A candle jar was used to mature the parasites at 37° C. for 35-56 hours. Incubation was stopped when >40% of ring stage parasites had reached the mature schizont stage in the drug-free control wells as determined by light microscopy.

Parasite growth was quantified by nucleic acid staining and data acquisition using flow cytometry as described in detail elsewhere[6]. Parasite growth was quantified for each drug concentration and normalised to the control well.

The dose-response data were analysed using nonlinear regression analysis and the half-maximal inhibition of growth ($IC_{50}$) value derived using an inhibitory sigmoid Emax model (In Vitro Analysis and Reporting Tool; $IVART_7$). Ex vivo $IC_{50}$ data were only used from predicted curves where the $E_{max}$ and $E_0$ were within 15% of 100 and 1, respectively.

(iii) Quality Control (QC) Procedures

Drug plate quality was assured by running schizont maturation assays with the chloroquine-resistant strain K1 and the chloroquine-sensitive strain FC27.

(iv) Results are summarized in table 3.

TABLE 3

| Compound No | IUPAC NAME | *P. falciparum* clinical field isolates, IC50 | *P. vivax* clinical field isolates, IC50 |
|---|---|---|---|
| 1b | 5-((3-(carbamimidoylcarbamoyl)-5-(trifluoromethyl)phenyl)ethynyl)-N-(pyridin-2-yl)-2-(trifluoromethyl) benzamide hydrochloride | 18.9 nM | 12 nM |

Drug susceptibility did not differ significantly between species for the standard anti-malarials piperaquine, mefloquine and artesunate and compound 1b. Therefore, the compound 1b appears to be an efficient candidate for treating malaria.

Indications

As illustrated in the examples, compounds of formula (I) according to the invention are able to significantly inhibit the activity of *Plasmodium falciparum* and/or *Plasmodium vivax*.

The compounds according to the invention can therefore be used to prepare medicaments, especially medicaments which inhibit the activity of *Plasmodium falciparum* and/or *Plasmodium vivax*.

Accordingly, in another of its aspects, the invention provides medicaments which comprise a compound of formula (I) or a pharmaceutically acceptable salt thereof.

These medicaments are employed therapeutically, especially in the treatment and/or the prophylaxis of malaria.

Pharmaceutical Compositions

According in another of its aspects, the present disclosure relates to pharmaceutical compositions comprising, as active principle, a compound of formula (I) according to the invention. More particularly, these pharmaceutical compositions contain an effective dose of at least one compound of formula (I) according to the invention and also at least one pharmaceutically acceptable carrier, diluent or excipient.

Thus, according to one embodiment, the present disclosure relates to pharmaceutical compositions comprising one compound of formula (I) or a pharmaceutically acceptable salt thereof according to the invention, and at least one pharmaceutically acceptable carrier, diluent or excipient thereof.

According to another embodiment, the present disclosure relates to pharmaceutical compositions comprising at least one compound of formula (I) or a pharmaceutically acceptable salt thereof according to the invention, and at least one pharmaceutically acceptable carrier, diluent or excipient thereof.

The said excipients are selected, in accordance with the pharmaceutical form and method of administration desired, from the customary excipients, which are known to a person skilled in the art.

In the pharmaceutical compositions of the present invention for oral, sublingual, subcutaneous, intramuscular, intravenous, topical, local, intra-tracheal, intranasal, transdermal or rectal administration, the active principle of formula (I) above, or its salt, may be administered in a unit administration form, in a mixture with conventional pharmaceutical excipients, to animals and to human beings for the proxylaxis or treatment of malaria.

Unit Administration

The unit administration forms appropriate include oral forms such as tablets, soft or hard gel capsules, powders, granules and oral solutions or suspensions, sublingual, buccal, intratracheal, intra-ocular and intranasal administration forms, forms for inhalative, topical, transdermal, subcutaneous, intra-muscular or intravenous administration, rectal administration forms and implants. For topical application it is possible to use the compounds according to the invention in creams, gels, ointments or lotions.

As an example, a unit administration form of a compound according to the invention in tablet form may comprise the following components:

| | |
|---|---:|
| Compound of formula (I) according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

Dosage

There may be particular cases in which high or low dosages are appropriate; such dosages do not depart from the scope of the invention. According to usual practice, the dosage that is appropriate for each patient is determined by the doctor according to the mode of administration and the weight and response of the said patient.

For instance, the dosage administered—as single or multiple doses—to an individual will vary depending upon a variety of factors, including pharmacokinetic properties, patient conditions and characteristics (sex, age, body weight, health, size), extent of symptoms, concurrent treatments, frequency of treatment and the effect desired.

Combination

For treating malaria and to prevent resistance—the World Health Organization recommends—as stated in the 'Guidelines for treatment of Malaria, third edition, ISBN 978 92 4 154912 7—to use combination with at least two effective antimalarial compounds with different mechanism of action.

Accordingly, in another of its aspects, the compounds of formula (I) according to the invention will be part of combination treatments comprising the administration of two or more antimalarial compounds with unrelated mechanism of actions. Such a combination of at least one compound (I) according to the invention and at least one other anti-malaria active principle(s) (different from a compound of formula (I)) can be comprised either in the same galenic formulation for example, such as the one disclosed previously, or in different galenic formulations.

According to an embodiment, when this combination is comprised in the same galenic formulation, the combination is preferably a fixed-dose combination in which at least one compound (I) and at least one other anti-malaria active principle (distinct from a compound (I)) can be formulated together for example in the same tablet, capsule, powder, suspension or granule.

According to another embodiment, when this combination is comprised in different galenic formulations, the administration of each of these active principles can be simultaneous or sequential.

Thus, according to another aspect, the disclosure further relates to a combination of at least one compound of formula (I) according to the disclosure or a pharmaceutically acceptable salt thereof and of at least one other anti-malaria active principle different from a compound of formula (I) as defined in the present disclosure.

The disclosure further relates to a pharmaceutical composition comprising at least one combination according to the disclosure, and at least one pharmaceutically acceptable carrier, diluent or excipient thereof.

The disclosure further relates to a combination according to the disclosure for use as a medicament, such as for use in the prevention and/or treatment of malaria.

The disclosure further relates to a combination according to the disclosure for use in the treatment and/or prevention of infections of blood cells infected with *Plasmodium falciparum* and/or *Plasmodium vivax*. According to a particular embodiment, the infection is malaria.

Thus, the disclosure further relates to a method for preventing and/or treating malaria in a patient in need thereof that comprises at least the administering of a combination according to the disclosure in a patient in need thereof.

Method of Treatment

The present invention, according to another of its aspects, also provides a method of treating the pathologies indicated above, which comprises administering to a patient an effective dose of a compound according to the invention, or one of its pharmaceutically acceptable salts, or of a combination according to the disclosure.

The invention claimed is:

1. A compound of formula (I):

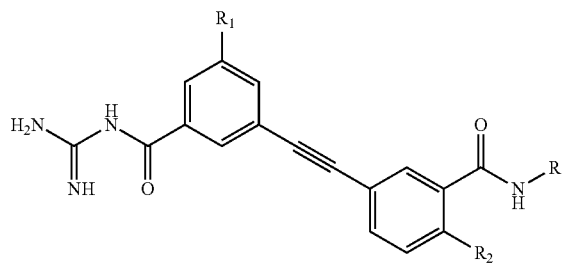

Formula (I)

wherein:
$R_1$ is a fluorine atom or a perhalogeno linear alkyl radical containing 1, 2 or 3 carbon atoms,
$R_2$ is a chlorine atom; a linear alkyl radical containing 1, 2 or 3 carbon atoms optionally substituted with at least one fluorine atom; or a perhalogeno linear alkyl radical containing 1, 2 or 3 carbon atoms, and
R is a hydrogen atom or a radical of formula (Ia)

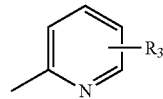

Formula (Ia)

$R_3$ is a hydrogen atom; a hydroxyl radical; or a linear or branched alkyl radical containing 1, 2 or 3 carbon atoms,
and $R_3$ is in position 5 or in position 6 of said radical of formula (Ia),
or a pharmaceutically acceptable salt thereof.

2. The compound according to claim 1, wherein $R_1$ is a fluorine atom or a trifluoromethyl radical.

3. The compound according to claim 1, wherein $R_2$ is a chlorine atom, a methyl radical or a perhalogeno linear alkyl radical containing 1, 2 or 3 carbon atoms.

4. The compound according to claim 1, wherein R is the radical of formula (Ia).

5. The compound according to claim 1, wherein R is a radical of formula (Ia) and $R_3$ is in position 5 or 6 of said radical of formula (Ia).

6. The compound according to claim 1, wherein R is the radical of formula (Ia) and $R_3$ is a hydrogen atom, a hydroxyl radical or a methyl radical.

7. The compound according to claim 5, wherein R is the radical of formula (Ia) and $R_3$ is a hydroxyl radical in position 5 of said radical of formula (Ia).

8. The compound according to claim 5, wherein R is the radical of formula (Ia) and $R_3$ is a linear or branched alkyl radical containing 1, 2 or 3 carbon atoms in position 6 of said radical of formula (Ia).

9. The compound according to claim 1, wherein at least one of R₁ and R₂ is a perfluoromethyl radical.

10. The compound according to claim 1, wherein both R₁ and R₂ are a perfluoromethyl radical.

11. The compound according to claim 1, said compound being selected from:
- 5-((3-(carbamimidoylcarbamoyl)-5-(trifluoromethyl)phenyl)ethynyl)-N-(pyridin-2-yl)-2-(trifluoromethyl)benzamide,
- 5-((3-(carbamimidoylcarbamoyl)-5-(trifluoromethyl)phenyl)ethynyl)-N-(pyridin-2-yl)-2-(trifluoromethyl)benzamide,
- 5-((3-(carbamimidoylcarbamoyl)-5-(trifluoromethyl)phenyl)ethynyl)-N-(pyridin-2-yl)-2-(trifluoromethyl)benzamide,
- 5-((3-((diaminomethylene)carbamoyl)-5-(trifluoromethyl)phenyl)ethynyl)-2-methyl-N-(6-methylpyridin-2-yl)benzamide,
- 5-((3-(carbamimidoylcarbamoyl)-5-fluorophenyl)ethynyl)-N-(6-methylpyridin-2-yl)-2-(trifluoromethyl)benzamide,
- 5-((3-(carbamimidoylcarbamoyl)-5-trifluoromethyl)phenyl)ethynyl)-2-methyl-N-(pyridin-2-yl)benzamide,
- 5-((3-(carbamimidoylcarbamoyl)-5-(trifluoromethyl)phenyl)ethynyl)-N-(5-hydroxypyridin-2-yl)-2-(trifluoromethyl)benzamide,
- 5-((3-(carbamimidoylcarbamoyl)-5-(trifluoromethyl)phenyl)ethynyl)-2-chloro-N-(pyridin-2-yl)benzamide,
- 5-((3-(carbamimidoylcarbamoyl)-5-fluorophenyl)ethynyl)-N-(pyridin-2-yl)-2-(trifluoromethyl)benzamide,
- N-carbamimidoyl-3-((3-carbamoyl-4-(trifluoromethyl)phenyl)ethynyl)-5-trifluoromethyl)benzamide, and
- their pharmaceutically acceptable salts.

12. The compound according to claim 1, said compound being selected from:
- 5-((3-(carbamimidoylcarbamoyl)-5-(trifluoromethyl)phenyl)ethynyl)-N-(pyridin-2-yl)-2-(trifluoromethyl)benzamide hydrochloride,
- 5-((3-(carbamimidoylcarbamoyl)-5-(trifluoromethyl)phenyl)ethynyl)-N-(pyridin-2-yl)-2-(trifluoromethyl)benzamide malonic acid,
- 5-((3-((diaminomethylene)carbamoyl)-5-(trifluoromethyl)phenyl)ethynyl)-2-methyl-N-(6-methylpyridin-2-yl)benzamide hydrochloride,
- 5-((3-(carbamimidoylcarbamoyl)-5-fluorophenyl)ethynyl)-N-(6-methylpyridin-2-yl)-2-(trifluoromethyl)benzamide hydrochloride,
- 5-((3-(carbamimidoylcarbamoyl)-5-trifluoromethyl)phenyl)ethynyl)-2-methyl-N-(pyridin-2-yl)benzamide hydrochloride,
- 5-((3-(carbamimidoylcarbamoyl)-5-(trifluoromethyl)phenyl)ethynyl)-N-(5-hydroxypyridin-2-yl)-2-(trifluoromethyl)benzamide hydrochloride,
- 5-((3-(carbamimidoylcarbamoyl)-5-(trifluoromethyl)phenyl)ethynyl)-2-chloro-N-(pyridin-2-yl)benzamide hydrochloride,
- 5-((3-(carbamimidoylcarbamoyl)-5-fluorophenyl)ethynyl)-N-(pyridin-2-yl)-2-(trifluoromethyl)benzamide hydrochloride, and
- pharmaceutically acceptable salts thereof.

13. A composition comprising at least one compound according to claim 1 or a pharmaceutically acceptable salt thereof and of at least one other anti-malaria active principle different from said at least one compound.

14. A pharmaceutical composition comprising at least one compound according to claim 1 or a pharmaceutically acceptable salt thereof and at least one pharmaceutically acceptable carrier, diluent or excipient thereof.

15. A method of treating malaria in a patient in need thereof that comprises administering of a compound according to claim 1 or a pharmaceutically acceptable salt thereof or a composition comprising said compound or pharmaceutically active salt to a patient having malaria.

* * * * *

UNITED STATES PATENT AND TRADEMARK OFFICE
CERTIFICATE OF CORRECTION

Page 1 of 2

PATENT NO. : 11,078,160 B2
APPLICATION NO. : 16/628720
DATED : August 3, 2021
INVENTOR(S) : Cécile Pascal et al.

It is certified that error appears in the above-identified patent and that said Letters Patent is hereby corrected as shown below:

In the Specification

Column 28,
Lines 64-66, "5-(3-(carbamimidoylcarbamoyl)-5-(trifluoromethyl)phenyl)ethynyl)-N-(pyridin-2-yl)-2-(trifluoromethyl)benzamide" should read --5-((3-(carbamimidoylcarbamoyl)-5-(trifluoromethyl)phenyl)ethynyl)-N-(pyridin-2-yl)-2-(trifluoromethyl)benzamide--.

Column 29,
Line 51, "NH4OH" should read --NH$_4$OH--.

Column 42,
Line 15, "HCl dioxane" should read --concentrated HCl--.

Column 45,
Lines 30-40, " 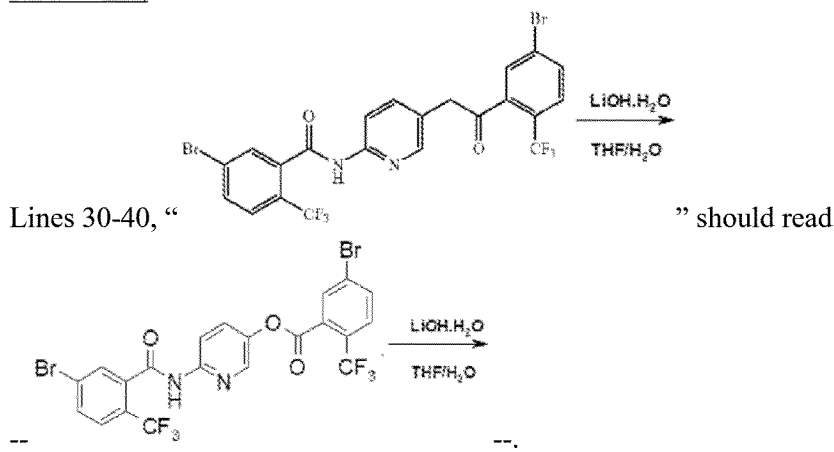 " should read -- -- .

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*

Column 55,
Line 26, " 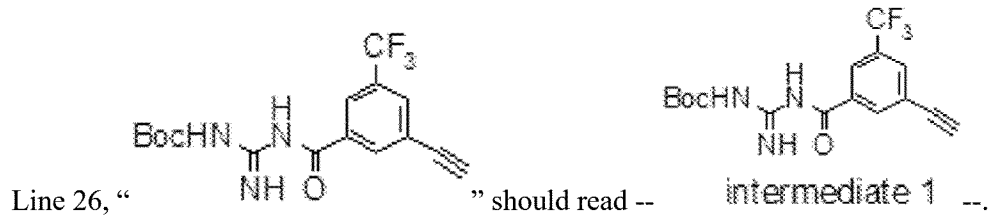 " should read -- intermediate 1 --.
Column 55,
Line 29, "EtOAc, 60° C., 3 h" should read --EtOAc, 60° C., 5h--.